(12) United States Patent
Takenaka

(10) Patent No.: US 11,571,141 B2
(45) Date of Patent: Feb. 7, 2023

(54) WALKING SUPPORT SYSTEM, WALKING SUPPORT METHOD, AND WALKING SUPPORT PROGRAM

(71) Applicant: HONDA MOTOR CO., LTD., Tokyo (JP)

(72) Inventor: Toru Takenaka, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 614 days.

(21) Appl. No.: 16/495,595

(22) PCT Filed: Feb. 28, 2018

(86) PCT No.: PCT/JP2018/007465
§ 371 (c)(1),
(2) Date: Sep. 19, 2019

(87) PCT Pub. No.: WO2018/180144
PCT Pub. Date: Oct. 4, 2018

(65) Prior Publication Data

US 2020/0008712 A1  Jan. 9, 2020

(30) Foreign Application Priority Data

Mar. 29, 2017  (JP) .............................. JP2017-064853

(51) Int. Cl.
*A61B 5/11* (2006.01)
*A61H 1/02* (2006.01)
*A63B 24/00* (2006.01)

(52) U.S. Cl.
CPC .................. *A61B 5/11* (2013.01); *A61H 1/02* (2013.01); *A61B 2562/0219* (2013.01);
(Continued)

(58) Field of Classification Search
CPC ... A61B 5/11; A61B 2562/219; A61B 5/6895; A61B 5/1038; A61B 2505/09;
(Continued)

(56) References Cited

U.S. PATENT DOCUMENTS 7,190,141 B1 * 3/2007 Ashrafiuon ............ B25J 9/0006
318/568.14
2004/0059264 A1  3/2004 Nishibe et al.
(Continued)

FOREIGN PATENT DOCUMENTS

CN          1914009 A       2/2007
CN        104197932 A      12/2014
(Continued)

OTHER PUBLICATIONS

PCT/ISA/210 from International Application PCT/JP2018/007465 with the English translation thereof.
(Continued)

*Primary Examiner* — Patrick Fernandes
(74) *Attorney, Agent, or Firm* — Carrier Shende & Associates, P.C.; Joseph P. Carrier; Jeffrey T. Gedeon

(57) ABSTRACT

A walking support system includes: an information output device (260); a motion detector (220) which detects a motion of a user; a foot landing position detector (230) which detect a foot landing position of the user; a determiner (240) which determines a recommended foot landing position which is a landing position of the feet suitable for stabilizing motions of a gait of the user on the basis of motions of a gait of the user detected by the motion detector, the foot landing position detected by the foot landing position detector, and dynamics; and an output controller (250) which outputs information indicating the recommended foot landing position determined by the determiner to the information output device.

9 Claims, 17 Drawing Sheets

(52) U.S. Cl.
CPC ............... *A61H 2201/164* (2013.01); *A63B 2024/0012* (2013.01); *A63B 2220/44* (2013.01); *A63B 2225/50* (2013.01)

(58) Field of Classification Search
CPC ....... A61B 5/112; A61B 5/11224; A61H 1/02; A61H 2201/164; A61H 1/0255; A61H 1/0262; A63B 2024/0012; A63B 2220/44; A63B 2225/50; G06V 40/23; G16H 20/70; G16H 20/30; B25J 9/0006
See application file for complete search history.

(56) References Cited

U.S. PATENT DOCUMENTS

| | | | | |
|---|---|---|---|---|
| 2012/0172770 | A1* | 7/2012 | Almesfer | A61H 1/0255 601/23 |
| 2014/0148931 | A1 | 5/2014 | Watanabe et al. | |
| 2015/0294481 | A1* | 10/2015 | Sakaue | G06V 40/23 600/595 |
| 2015/0324637 | A1* | 11/2015 | Utsunomiya | G16H 20/70 382/107 |
| 2017/0065849 | A1* | 3/2017 | Konishi | A61B 5/6895 |

FOREIGN PATENT DOCUMENTS

| | | |
|---|---|---|
| JP | 2003164544 A | 6/2003 |
| JP | 2006-204730 A | 8/2006 |
| JP | 2007-283474 A | 11/2007 |
| JP | 2008-080418 A | 4/2008 |
| JP | 2009-240775 A | 10/2009 |
| JP | 2011-229838 A | 11/2011 |
| JP | 2017-051365 A | 3/2017 |
| WO | 2010/039674 A2 | 4/2010 |
| WO | 2013/129606 A1 | 9/2013 |

OTHER PUBLICATIONS

Takenaka et al., "Real-time Walking Gait Generation for Biped Robot", The Robotics Society of Japan, 2011, vol. 29, No. 5, pp. 455-462.

Kurematsu et al., "Trajectory Planning of a Biped Locomotive Robot: Combination of an Inverted Pendulum and the Neural Network", Transactions of the Institute of Systems, Control and Information Engineers, 1989, vol. 2, No. 4, pp. 118-127.

Chinese Office Action, dated Jan. 15, 2021, issued over the corresponding Chinese Patent Application No. 201880015672.6 and English translation of the Search Report portion only.

* cited by examiner

WALKING SUPPORT SYSTEM, WALKING SUPPORT METHOD, AND WALKING SUPPORT PROGRAM

TECHNICAL FIELD

The present invention relates to a walking support system, a walking support method, and a walking support program.

Priority is claimed on Japanese Patent Application No. 2017-64853, filed Mar. 29, 2017, the content of which is incorporated herein by reference.

BACKGROUND ART

Conventionally, a technology for acquiring body motion information from a user who is walking or running on a movable surface of a treadmill or the like and displaying target indicators for the position of the feet on the movable surface or outputting a score with respect to a motion posture on the basis of the acquired body motion information is known (refer to Patent Literature 1 and 2, for example).

CITATION LIST

Patent Literature

[Patent Literature 1]
Japanese Unexamined Patent Application, First Publication No. 2009-240775
[Patent Literature 2]
PCT International Publication No. WO 2013/129606

SUMMARY OF INVENTION

Technical Problem

In the method of this conventional technology, the position at which the feet land may not be indicated with strides and at times suitable for a user. Accordingly, motions for a walk of a user may not be able to be suitably guided.

An object of the present invention devised in view of the aforementioned circumstances is to provide a walking support system, a walking support method, and a walking support program which can properly guide motions of a gait of a user.

Solution to Problem (1): A walking support system includes: an information output device; a motion detector which detects a motion of a user; a foot landing position detector which detect a landing position of the foot of the user; a determiner which determines a recommended foot landing position which is a foot landing position for the feet suitable for stabilizing motions of a gait of the user on the basis of motions of a gait of the user detected by the motion detector, the foot landing position detected by the foot landing position detector, and dynamics thereof; and an output controller which outputs information indicating the recommended foot landing position determined by the determiner to the information output device.

(2): In (1), the dynamics may be a dynamic model including an inverted pendulum representing motions of an upper body or a centroid in the horizontal direction, and the determiner determines a recommended foot landing position of the user such that motions of the user converge on a predetermined motion on the basis of motions of a gait of the user, the foot landing position and the dynamic model.

(3): In (2), the predetermined motion may be a steady-state gait.

(4): In (1), the determiner may continuously determine a recommended foot landing position in the case of foot landing at a current time.

(5): In (1), the determiner may determine a recommended foot landing position using a map or a neural network obtained according to deep learning.

(6): In (1), a support device which supports motions of the feet of the user, and a support controller which guides the feet of the user to the recommended foot landing position through the support device may be further included.

(7): In (1), an orientation detector which detects orientations of the feet of the user with respect to a reference direction when the feet of the user have landed may be further included, and the determiner may determine the recommended foot landing position such that a trajectory of a centroid of the body of the user is turned in response to orientations of the feet on the basis of the orientations detected by the orientation detector.

(8): In (1), the determiner may correct a recommended foot landing position determined on the basis of the movement velocity, the foot landing position and the dynamics to a position closer to the user when a current movement velocity of the user is accelerated, and correct the recommended foot landing position determined on the basis of the movement velocity, the foot landing position and the dynamics to a position further away from the user when the current movement velocity of the user is decelerated.

(9): In (1), an operation receptor which receives an operation from the user may be further included, and the determiner may switch display modes and determine the recommended foot landing position on the basis of details of an operation received by the operation receptor.

(10): A walking support method, using a computer, includes: detecting a motion of a user; detecting a foot landing position of the user; determining a recommended foot landing position which is a foot landing position for the feet suitable for stabilizing motions of a gait of the user on the basis of detected motions of a gait of the user, the detected foot landing position, and dynamics; and outputting information indicating the determined recommended foot landing position to an information output device.

(11): A non-transitory computer-readable storage medium that stores a walking support program to be executed by a computer to perform at least: detecting a motion of a user; detecting a foot landing position of the user; determining a recommended foot landing position which is a foot landing position for the feet suitable for stabilizing motions of a gait of the user on the basis of detected motions of a gait of the user, the detected foot landing position, and dynamics; and outputting information indicating the determined recommended foot landing position to an information output device.

Advantageous Effects of Invention

According to (1) to (5), (10) or (11), the walking support system can properly guide motions of a gait of a user.

According to (6), the walking support system can guide a user's feet to recommended foot landing positions through a support device. Accordingly, the user can easily land on their feet close to the recommended foot landing positions.

According to (7), a user can achieve a smooth turning gait in an intended direction.

According to (8) or (9), the walking support system can display recommended foot landing positions in a mode associated with a user.

DESCRIPTION OF EMBODIMENTS

Hereinafter, embodiments of a walking support system, a walking support method, and a walking support program of the present invention will be described with reference to the drawings.

First Embodiment

Figure 1:
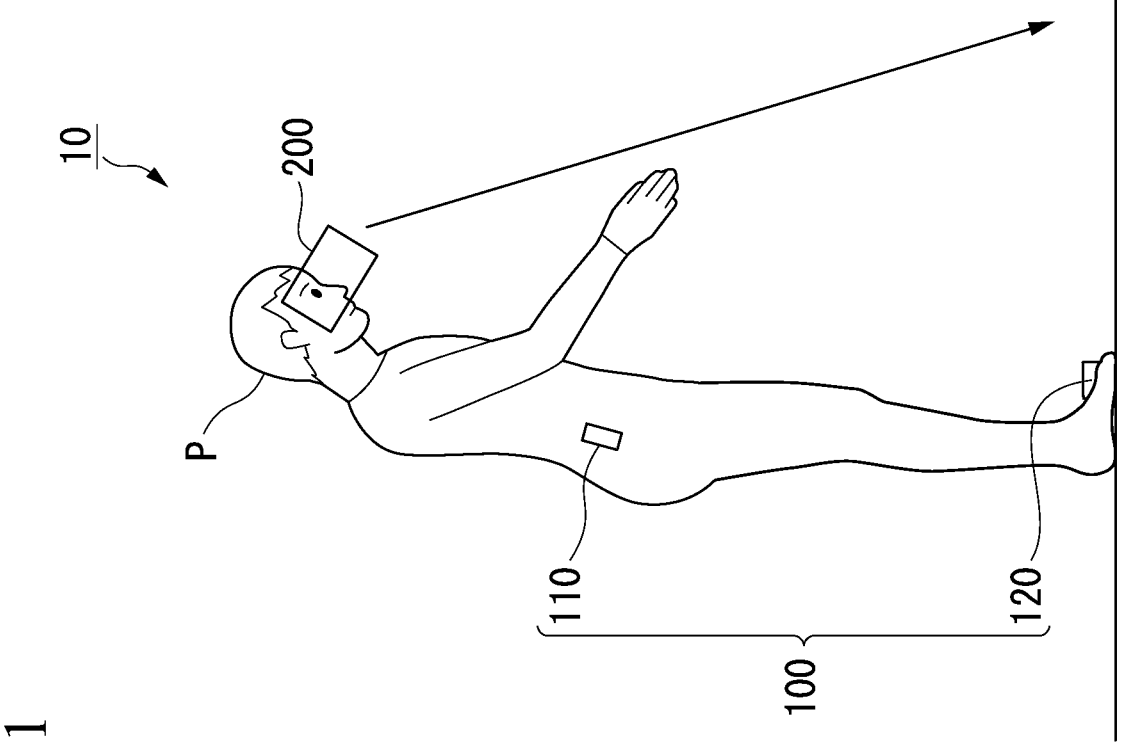
FIG. 1 is a schematic diagram showing a walking support system 10 of a first embodiment.

FIG. 1 is a schematic diagram showing a walking support system 10 of a first embodiment. The walking support system 10 includes, for example, a motion information detector 100 and a display device 200. The motion information detector 100 detects information about a motion (e.g., a motion of a gait) of a user P. The motion information detector 100 includes, for example, an upper body information detector 110 and a foot information detector 120. The upper body information detector 110, the foot information detector 120 and the display device 200 are connected such that they can communicate in a wired or wireless manner, for example.

At least one upper body information detector 110 is attached to the upper body of the user P using the walking support system 10. The upper body information detector 110 may include an acceleration sensor and an angular acceleration sensor, for example, and detect the position, velocity and orientation of the upper body of the user P by performing a predetermined calculation process such as a strapdown method on the basis of detection results of the acceleration sensor and the angular acceleration sensor. At least one foot information detector 120 is attached to the left and right feet of the user P. The foot information detector 120 may include an acceleration sensor and an angular acceleration sensor, for example, and detect the positions, velocities and orientations of the left and right feet of the user P by performing a predetermined calculation process such as a strapdown method on the basis of detection results of the acceleration sensor and the angular acceleration sensor.

The display device 200 is, for example, an augmented reality (AR) device which displays additional information overlaid on a real space visually recognized by the user P. The display device 200 may be a virtual reality (VR) device which displays a virtual reality. The display device 200 is, for example, a glasses-type display or a head mount display mounted on the head of the user P. The display device 200 determines recommended foot landing positions of the feet of the user P on the basis of accelerations and orientations detected by the upper body information detector 110 and the foot information detector 120 and outputs information corresponding to the determined recommended foot landing positions.

Figure 2:
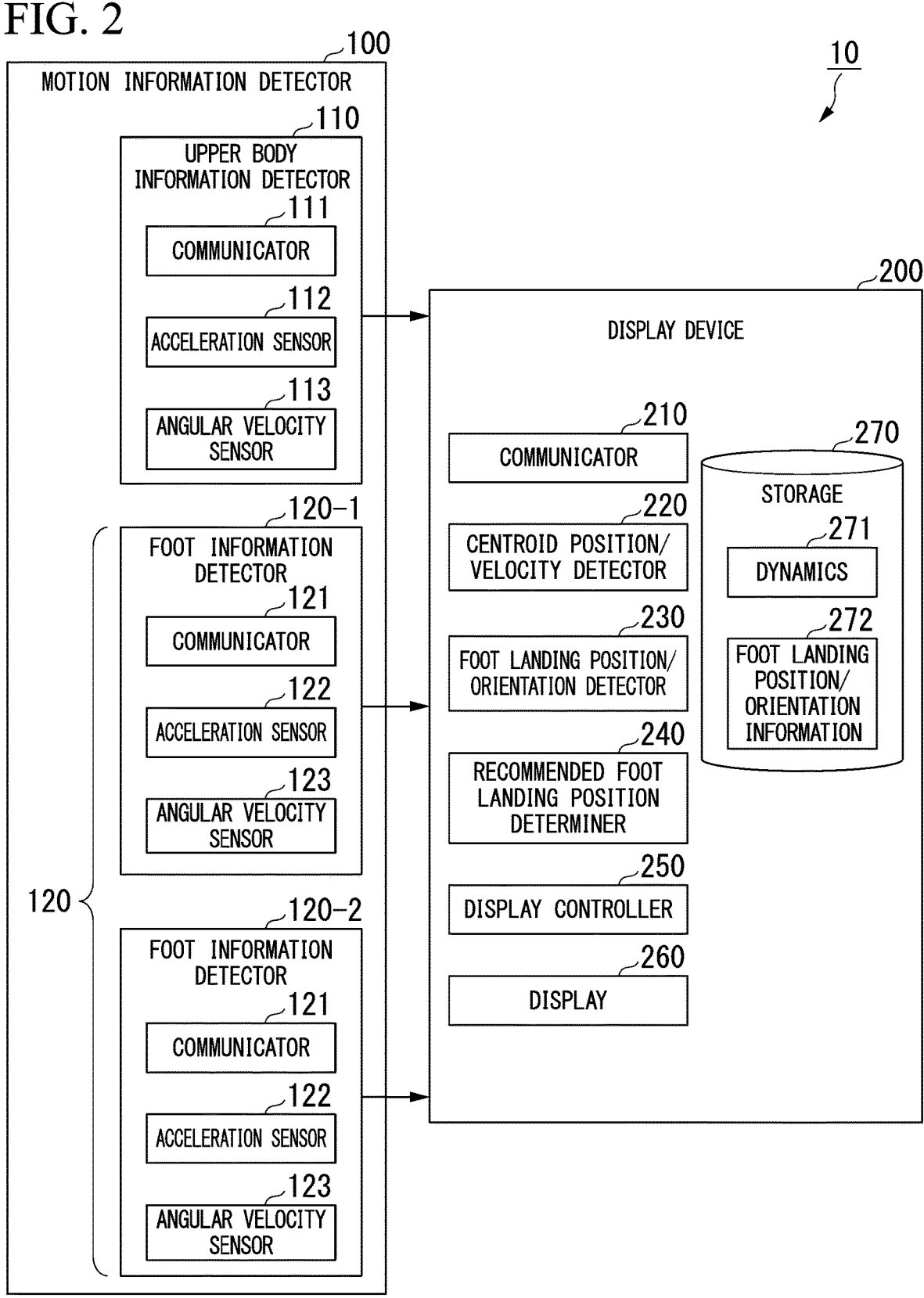
FIG. 2 is a diagram showing an example of a functional configuration of the walking support system 10 of the first embodiment.

FIG. 2 is a diagram showing an example of a functional configuration of the walking support system 10 of the first embodiment. The upper body information detector 110 includes, for example, a communicator 111, an acceleration sensor 112, and an angular velocity sensor 113. The acceleration sensor 112 detects an acceleration of the upper body of the user P. The angular velocity sensor 113 detects an angular velocity (e.g., inclination) of the upper body of the user P. The upper body information detector 110 derives the position, velocity and orientation of the upper body of the user P on the basis of information detected by the acceleration sensor 112 and the angular velocity sensor 113. The communicator 111 includes a communication interface for performing communication between apparatuses through a wired or wireless network and communicates with a communicator 121 of the display device 200. The communicator 111 outputs the position, velocity and orientation of the upper body of the user P derived by the upper body information detector 110 to the communicator 121.

The foot information detector 120 includes foot information detectors 120-1 and 120-2 attached to the left and right legs of the user P. Each of the foot information detectors 120-1 and 120-2 includes a communicator 121, an acceleration sensor 122 and an angular velocity sensor 123. The acceleration sensor 122 detects an acceleration of the foot to which it is attached. The angular velocity sensor 123 detects an angular velocity of the foot to which it is attached. The foot information detector 120 derives the positions, velocities and orientations of the feet of the user P on the basis of information detected by the acceleration sensor 122 and the angular velocity sensor 123. The communicator 121 includes a communication interface for performing communication between apparatuses through a wired or wireless network and communicates with the communicator 121 of the display device 200. The communicator 121 outputs the positions, velocities and orientations of the feet of the user P derived by the foot information detector 120 to the communicator 121.

The motion information detector 100 may include, for example, a camera device which captures a motion of the user P as another variation. In this case, the motion information detector 100 acquires capture data with respect to the user P from the camera device installed in an external environment and detects the positions and orientations of the upper body and the feet of the user P on the basis of the acquired capture data. The motion information detector 100 may be a joint angle sensor attached to respective joints (at least a hip joint and a knee) of the user P as another variation. The motion information detector 100 may be a posture sensor including an acceleration sensor and an angular velocity sensor (and a geomagnetic sensor) which is attached to respective parts of the body of the user P, such as the leg, thigh and upper body, as another variation. The motion information detector 100 may be a magnetic relative position sensor which detects a relative positional relationship between the upper body and the feet of the user P through a magnetic field generation device attached to the upper body of the user P and a magnetic sensor attached to the feet of the user P as another variation. The motion information detector 100 may be a combination of all or some of the above-described variations.

The display device 200 includes, for example, the communicator 210, a centroid position/velocity detector 220, a foot landing position/orientation detector 230, a recommended foot landing position determiner 240, a display controller 250, a display 260, and a storage 270. The centroid position/velocity detector 220, the foot landing position/orientation detector 230, the recommended foot landing position determiner 240, and the display controller 250 are realized, for example, by a hardware processor such as a central processing unit (CPU) executing a program (software). All or some of these components may be realized by hardware (circuit part including circuitry) such as a large scale integration (LSI) circuit, an application specific integrated circuit (ASIC), a field-programmable gate array (FPGA), and a graphics processing unit (GPU) or realized by software and hardware in cooperation. The program may be stored in a storage device such as a hard disk drive (HDD) or a flash memory in advance or stored in a separable storage medium such as a DVD or a CD-ROM and installed in the storage when the storage medium is inserted into a drive device. A combination of the motion information detector 100 and the centroid position/velocity detector 220 is an example of a "motion detector." The foot landing position/orientation detector 230 is an example of a "foot landing position detector" and "orientation detector." The recommended foot landing position determiner 240 is an example of a "determiner." The display controller 250 is an example of an "output controller." The display 260 is an example of an "information output device."

The communicator 210 includes a communication interface for performing communication between apparatuses through a wired or wireless network and communicates with the communicator 111 of the upper body information detector 110 and the communicator 121 of the foot information detector 120.

The centroid position/velocity detector 220 detects a centroid position and a velocity of the user P on the basis of the position and velocity of the upper body detected by the upper body information detector 110 in the motion information detector 100 and the positions and velocities of the left and right feet detected by the foot information detectors 120-1 and 120-2 in the motion information detector 100. For example, the centroid position/velocity detector 220 sets weighted average values of the position and velocity of each part acquired by each detector as a centroid position and velocity. When the upper body information detector 110 is provided close to the centroid of the user P, the centroid position/velocity detector 220 may set a movement velocity calculated by performing integral operation processing on accelerations detected by the upper body information detector 110 as a centroid movement velocity. The centroid position/velocity detector 220 may calculate a centroid position by performing integral operation processing on the centroid movement velocity.

The foot landing position/orientation detector 230 detects foot landing positions and orientations of the feet in a gait (body movement while walking) of the user P. Specifically, the foot landing position/orientation detector 230 detects a timing at which an acceleration acquired by the acquired acceleration sensor 122 indicates a peak, for example, as a timing at which a foot of the user lands. The foot landing position/orientation detector 230 calculates a foot landing position from positions of the feet of the user P at the foot landing times. The foot landing position/orientation detector 230 detects orientations of the feet with respect to a reference direction at the foot landing timing as foot landing orientations. The foot landing position/orientation detector 230 stores the detected foot landing positions and orientations of the feet in the storage 270 as foot landing position/orientation information 272.

The recommended foot landing position determiner 240 determines foot landing positions to be recommended to the user P on the basis of a centroid movement velocity of the user P detected by the centroid position/velocity detector 220, foot landing positions and orientations of the feet of the user P detected by the foot landing position/orientation detector 230, and dynamics 271 stored in the storage 270. The dynamics 271 are, for example, dynamic modeling of a gait when a person is in motion using a linear inverted pendulum. Functions of the recommended foot landing position determiner 240 will be described in detail later.

The display controller 250 controls functions relating to image display of the display device 200. Specifically, the display controller 250 controls the display 260 such that the display 260 displays information indicating a recommended foot landing position determined by the recommended foot landing position determiner 240 at a predetermined timing. The information indicating a recommended foot landing position is an object image including a predetermined shape or the like, such as a foot shape, a rectangular shape, a circular shape or an oval shape, for example. A predetermined color or shape may be added to the object image, for example. The predetermined timing is, for example, a timing based on a past gait period of the user P. The predetermined timing may be a timing at which a foot is presumed to be separated from the ground or a timing at which an inclination of the upper body obtained by the angular velocity sensor 113 of the upper body information detector 110 has become an inclination equal to or greater than a predetermined value. The timing at which a foot is presumed to be separated from the ground is, for example, a timing at which an acceleration acquired from the acceleration sensor 122 of the foot information detector 120 becomes equal to or greater than a predetermined value upward. The predetermined timing may be a predetermined period. The predetermined period may be a whole period or the last half of a swing phase, for example.

The display 260 displays an object image indicating a recommended foot landing position on a display, for example, on the basis of control of the display controller 250. The display 260 may 2-dimensionally display the object image on a transmission type display or 3-dimensionally display the object image using a 3D display of a polarized glasses type or a liquid crystal shutter glasses type, or the like, for example. A specific example of the object image displayed on a screen of the display 260 will be described later.

The storage 270 includes, for example, an HDD, a flash memory, an electronically erasable programmable read only memory (EEPROM), a read only memory (ROM), a random access memory (RAM), or the like and stores various programs to be executed by a processor such as a CPU included in the display device 200, such as firmware and application programs, results of processing executed by the processor, and the like. For example, the dynamics 271 and the foot landing position/orientation information 272 are stored in the storage 270. The foot landing position/orientation information 272 is, for example, foot landing positions and orientations of the feet which correspond to several previous steps detected by the foot landing position/orientation detector 230.

<Regarding Dynamics 271>

Figure 3:
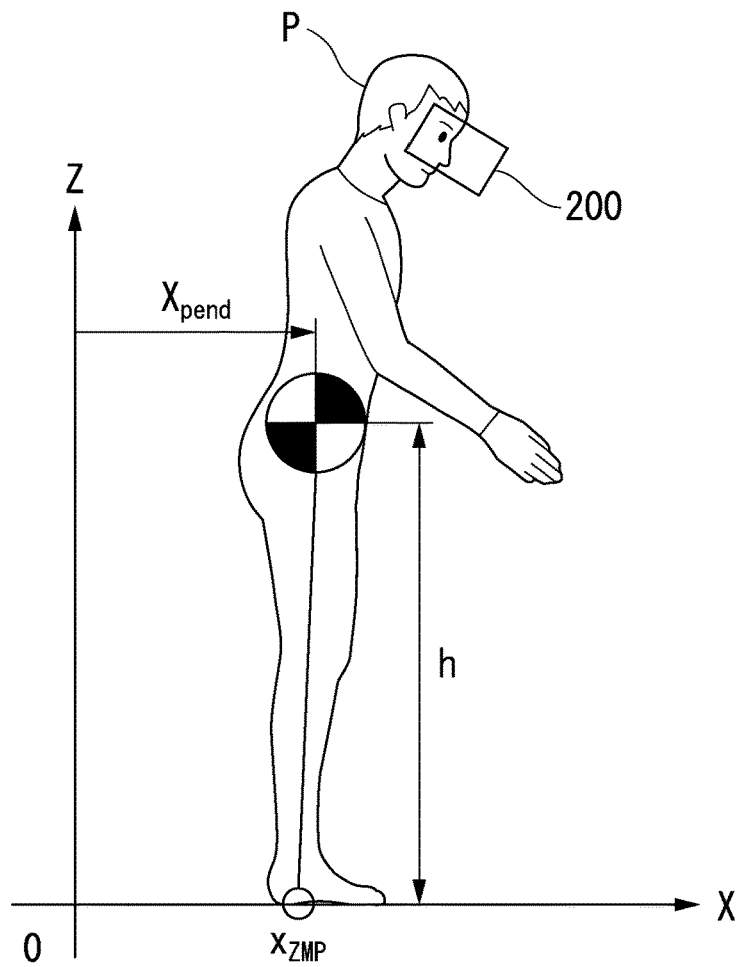
FIG. 3 is an explanatory diagram for dynamics 271.

Here, the dynamics 271 applied in the present embodiment will be described. FIG. 3 is a diagram for describing the dynamics 271. The dynamics 271 use a linear inverted pendulum with a constant material point height as a human dynamic model, for example. It is assumed that a horizontal position of the inverted pendulum material point represents a horizontal position of a representative point fixed to the upper body or a horizontal position of a fixed centroid. It is assumed that a motion on a sagittal plane and a motion on a lateral surface are independent of each other. It is assumed that a zero moment point (ZMP) position is set to a foot landing position (more specifically, a floor projection point of the ankle of a landing leg).

Here, when the horizontal position of the inverted pendulum is set to $X_{pend}$, the height (constant value) of the inverted pendulum is set to h, the ZMP position is set to $x_{ZMP}$, and the gravitational acceleration constant is set to g, a relationship of expression (1) is established between a motion of the material point of the linear inverted pendulum and the ZMP position.

[Math. 1]

$$\ddot{x}_{pend} = \frac{g}{h}(x_{pend} - x_{ZMP}) \quad (1)$$

Two black points indicated on the element of the left term of expression (1) represents a second order derivative value. When a positive eigenvalue of the inverted pendulum is set to $\lambda_0$, $\lambda_0$ is acquired by expression (2).

[Math. 2]

$$\lambda_0 = \sqrt{g/h} \quad (2)$$

Here, provisional values p and q are determined and represented as expression (3).

[Math. 3]

$$\begin{pmatrix} p \\ q \end{pmatrix} = \begin{pmatrix} 1 & -1/\lambda_0 \\ 1 & 1/\lambda_0 \end{pmatrix} \begin{pmatrix} x_{pend} \\ \dot{x}_{pend} \end{pmatrix} \quad (3)$$

In expression (3), a black point indicated on the lower element from among the elements of the column vector of the right term represents a derivative value. Expression (3) is converted into expression (4) using the provisional values p and q.

[Math. 4]

$$\frac{d}{dt}\begin{pmatrix} p \\ q \end{pmatrix} = \begin{pmatrix} -\lambda_0 & 0 \\ 0 & \lambda_0 \end{pmatrix}\begin{pmatrix} p \\ q \end{pmatrix} + \begin{pmatrix} \lambda_0 \\ -\lambda_0 \end{pmatrix} x_{ZMP} \quad (4)$$

When $x_{ZMP}$ is a constant value $x_{ZMP\_C}$, a general solution is expression (5).

[Math. 5]

$$\begin{pmatrix} p \\ q \end{pmatrix} = \begin{pmatrix} C_1 e^{-\lambda_0 t} + x_{ZMP\_c} \\ C_2 e^{\lambda_0 t} + x_{ZMP\_c} \end{pmatrix} \quad (5)$$

Here, C1 and C2 are any constants. That is, when they are time constants $1/\lambda_0$, p converges on an inverted pendulum supporting point position $x_{ZMP\_C}$, and q diverges. Due to these properties, p is called a convergence component and q is called a divergence component. Since the convergence component p naturally converges on the supporting point position, it is assumed that the convergence component p is ignored and only the divergence component q is considered for termination conditions.

Next, expression (6) is obtained according to expression (4).

[Math. 6]

$$q(t) = e^{\lambda_0 t} q(0) - \lambda_0 e^{\lambda_0 t} \int_0^t e^{-\lambda_0 \tau} x_{ZMP}(\tau) d\tau \quad (6)$$

That is, the divergence component q includes a divergence component initial value term and a target ZMP term. When a target ZMP is 0, it is ascertained that the divergence component q at an arbitrary time becomes $e^{\lambda_0 Ta}$ times after Ta (Ta≥0) seconds after the arbitrary time. This is called "property 1."

Next, a steady-state gait based on the conditions of aforementioned property 1 will be considered. The steady-state gait is 1 finishing motion (two continuous steps) and is a gait in which a relative positional relationship and a relative velocity between each foot and the inverted pendulum become continuous when a motion of a gait is repeated. The steady-state gait is a gait in which the relative positional relationship between each foot of the user P and the inverted pendulum and a rate of change of the relative positional relationship (that is, a relative velocity) in an initial stage are consistent with those at the end, for example. If each foot landing position and orientation and a target ZMP trajectory are set, a trajectory of a simple inverted pendulum model of the steady-state gait is primarily determined.

The steady-state gait is a gait in which periodic motions are continuously generated with the exception of movement amounts on the global coordinate system by alternately repeatedly generating a two-step gait (hereinafter, the first step is referred to as a "first steady-state gait" and the second step is referred to as a "second steady-state gait"). That is, an initial state and an end state of the steady-state gait must be consistent with each other except for positions and orientations on the global coordinate system. Hereinafter, this condition is called a "steady-state gait continuity condition."

Figure 4:
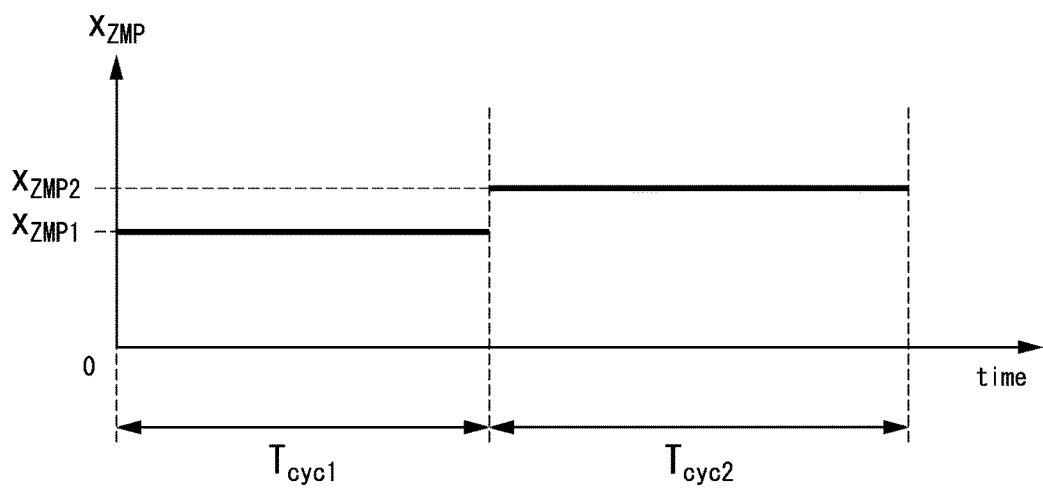
FIG. 4 is a diagram for describing a target foot landing position (target ZMP) of a steady-state gait and a gait period.

FIG. 4 is a diagram for describing a target foot landing position (target ZMP) of a steady-state gait and a gait period. The horizontal axis of FIG. 4 represents time and the vertical axis represents a ZMP position. When a target ZMP is 1 in a period from time 0 to time T, the influence of the target ZMP in this period on a divergence component at time T is set to R(T). Here, when $X_{ZMP}(t)=1$, R(t) is represented by expression (7) according to expression (6).

[Math. 7]

$$R(T) = -\lambda_0 e^{\lambda_0 T} \int_0^T e^{-\lambda_0 \tau} d\tau \qquad (7)$$
$$= -e^{\lambda_0 T}(1 - e^{-\lambda_0 T})$$

Here, when the initial time is set to 0, a period of the first steady-state gait is set to $T_{cyc1}$, a period of the second steady-state gait is set to $T_{cyc2}$, a target ZMP of the first steady-state gait is set to $X_{ZMP1}$, and a target ZMP of the second steady-state gait is set to $X_{ZMP2}$, as indicated by a target ZMP trajectory shown in FIG. 4, a value of the influence of the target ZMP of the first steady-state gait on a divergence component at the end of the second steady-state gait becomes $e^{\lambda_0 T2}$ times a value of the influence of the target ZMP of the first steady-state gait on a divergence component at the end of the first steady-state gait according to the aforementioned "property 1." Accordingly, a value $q_{cyc}^{ZMP}$ of the influence of the target ZMP trajectory of the whole period on a divergence component at the end of a steady-state gait is as represented by expression (8).

[Math. 8]

$$q_{cyc}^{ZMP} = e^{\lambda_0 T_2} x_{ZMP1} R(T_1) x_{ZMP2} R(T_2) \qquad (8)$$

A divergence component $q(t_E)$ at the end time of a steady-state gait is as represented by expression (9) according to expressions (6) and (8).

[Math. 9]

$$q(t_E) + e^{\lambda_0 t_E} q(0) + q_{cyc}^{ZMP} \qquad (9)$$

That is, an end divergence component of a steady-state gait can be analytically obtained on the basis of an initial divergence component and a ZMP trajectory. An initial divergence component of a steady-state gait can be analytically obtained from the aforementioned expressions and the steady-state gait continuity condition.

First Form Example of Recommended Foot Landing Position Determination Method

Next, a first form example of a recommended foot landing position determination method in the recommended foot landing position determiner 240 will be described in detail. First, terms and symbols to be used in the following description are defined. "A period of a stride" is a period from landing of one leg to landing of the opposite leg. A stride starting from the latest landing is referred to as a "current stride" and denoted by "Curr." A stride before the current stride is referred to as a "previous stride" and denoted by "B1." Further, a stride before the previous stride is referred to as a "stride before last" and denoted by "B2." A stride following the current stride is referred to as a "next stride" and denoted by "N1." Further, a stride next thereafter is referred to as a "stride after next" and denoted by "N2." Further, a stride next thereafter is referred to as a "second stride after next" and denoted by "N3." Further, a stride next thereafter is referred to as a "third stride after next" and denoted by "N4." A foot landing position in the initial stage of a gait is referred to as a "foot landing position of the gait." An orientation of landing (orientation of a landed foot) in the initial stage of a gait is referred to as an "orientation of landing of the gait." Foot landing positions of the gait before last (B2), the previous gait (B1), the current gait (Curr), the next stride (N1), the stride after next (N2), the second stride after next (N3) and the third stride after next (N4) are denoted by "P(B2), P(B1), P(Curr), P(N1), P(N2), P(N3), P(N4)." Orientations of foot landings of the stride before last (B2), the previous stride (B1), the current stride (Curr), the next stride (N1), the stride after next (N2), the second stride after next (N3) and the third stride after next (N4) are denoted by "S(B2), S(B1), S(Curr), S(N1), S(N2), S(N3), S(N4)." Periods (stride times) of the stride before last (B2), the previous stride (B1), the current stride (Curr), the next stride (N1), the stride after next (N2) and the second stride after next (N3) are denoted by "T(B2), T(B1), T(Curr), T(N1), T(N2), T(N3)."

Figure 5:
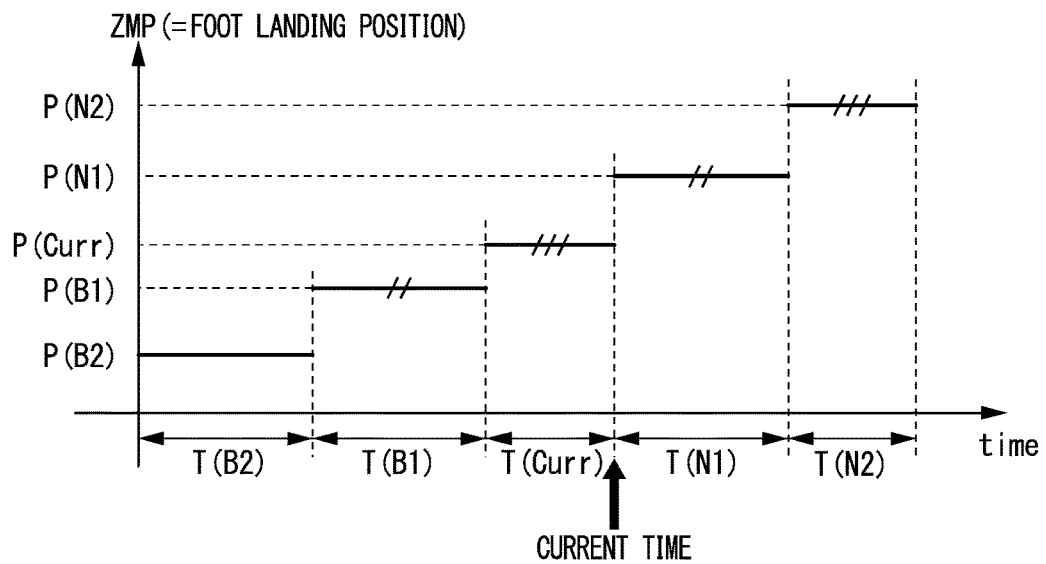
FIG. 5 is a diagram for describing a first form example of a recommended foot landing position determination method.

FIG. 5 is a diagram for describing the first form example of the recommended foot landing position determination method. The horizontal axis of FIG. 5 represents time and the vertical axis represents a ZMP (=foot landing position). FIG. 5 represents an example of a past ZMP trajectory and a target ZMP trajectory to be set from the present time. Although the target ZMP trajectory is represented as a one-dimensional trajectory in FIG. 5, the target ZMP trajectory is represented as a 2-dimensional or 3-dimensional trajectory in practice.

Figure 6:
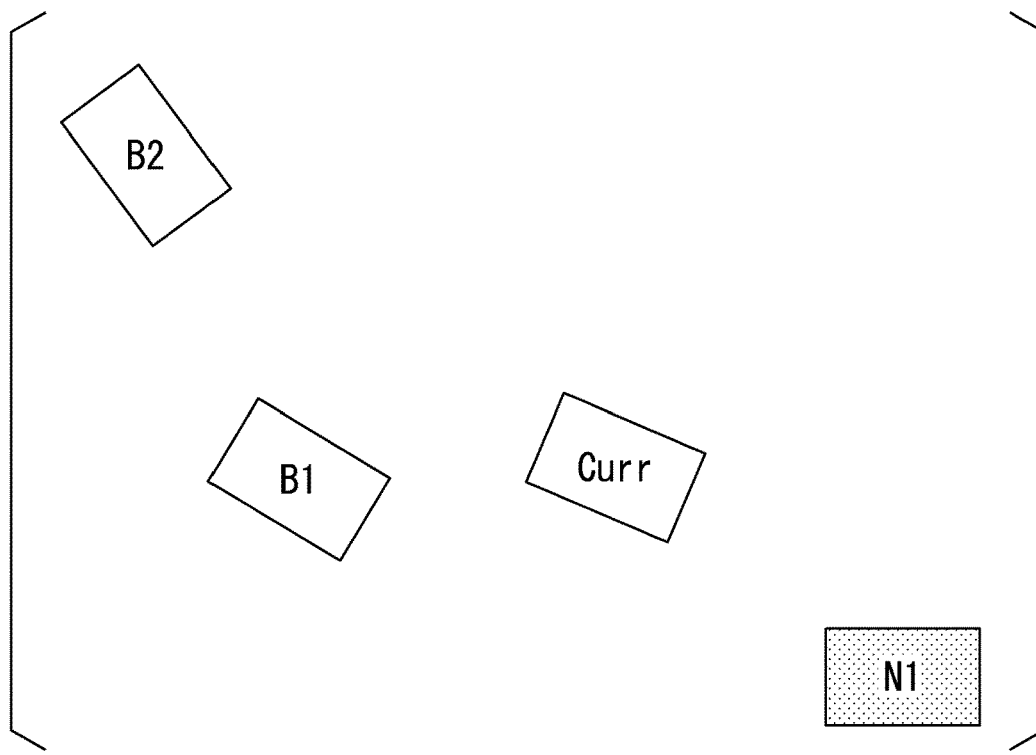
FIG. 6 is a diagram for describing recommended foot landing positions based on the first form example.

FIG. 6 is a diagram for describing a recommended foot landing position based on the first form example. In the example of FIG. 6, foot landing positions and orientations of the stride before last B2, the previous stride B1, the current stride Curr and the next stride N1 are represented using a rectangular shape.

First, the recommended foot landing position determiner 240 acquires foot landing positions (P(B2), P(B1) and P(Curr)), gait foot landing orientations (S(B2), S(B1) and S(Curr)) and gait periods (T(B2), T(B1) and T(Curr)) of the stride before last B2, the previous stride B1 and the current stride Curr through the foot information detector 120. In the present embodiment, the period T(Curr) of the current stride is a time from the latest landing time to the current time, as shown in FIG. 5. Next, the recommended foot landing position determiner 240 determines the foot landing position P(N1) and the orientation S(N1) of the next stride N1 on the basis of the gait foot landing positions (P(B2), P(B1) and P(Curr)) and the gait foot landing orientations (S(B2), S(B1) and S(Curr)).

Specifically, the recommended foot landing position determiner 240 determines the foot landing position P(N1) and the orientation S(N1) of the next stride N1 such that the stride before last B2, the previous stride B1, the current stride Curr and the next stride N1 become a steady-state gait.

For example, the recommended foot landing position determiner 240 determines the foot landing position and the orientation of the next stride N1 such that the foot landing position and the orientation of the next stride N1 based on the foot landing position and orientation of the current stride Curr are consistent with the foot landing position and the orientation of the previous stride B1 based on the foot landing position and orientation of the stride before last B2. The recommended foot landing position determiner 240 may determine recommended foot landing positions such that the trajectory of the centroid of the body of the user P turns in response to orientations of the feet on the basis of orientations detected by the foot landing position/orientation detector 230. Accordingly, a smooth turning gait can be performed in a direction intended by the user P.

Figure 7:
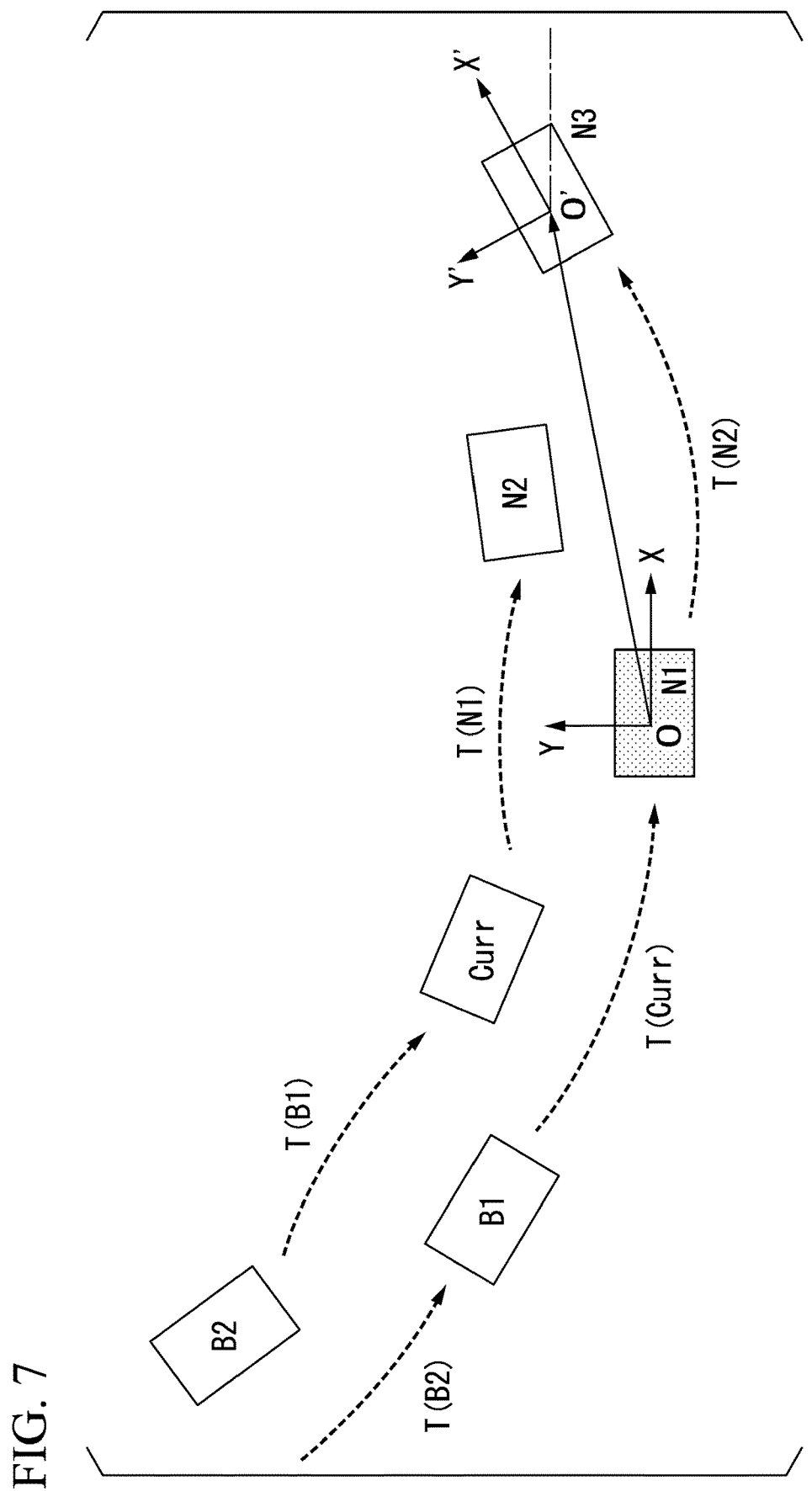
FIG. 7 is an explanatory diagram regarding a stride after the next stride which is provisionally set for recommended foot landing position determination.

FIG. 7 is a diagram for describing strides from the stride after next which are provisionally set for recommended foot landing position determination. In the example of FIG. 7, foot landing positions and orientations of the stride after next N2 and the second stride after next N3 are represented using a rectangular shape. The recommended foot landing position determiner 240 determines the foot landing positions P(N2) and P(N3) and the orientations S(N2) and S(N3) such that the current stride Curr, the next stride N1, the stride after next N2 and the second stride after next N3 become the same steady-state gaits as the stride before last B2, the previous stride B1, the current stride Curr and the next stride N1. That is, the recommended foot landing position determiner 240 determines the foot landing positions and the orientations of the strides N2 and N3 such that relative relationships of the foot landing positions and orientations of the strides B2, B1, Curr and N1 are consistent with relative relationships of the foot landing positions and orientations of the strides Curr, N1, N2 and N3.

Further, the recommended foot landing position determiner 240 makes the period T(N1) of the next stride N1 consistent with the period T(B1) of the previous stride B1 and makes the period T(N2) of the stride after next N2 consistent with the period T(Curr) of the current stride Curr, as shown in FIG. 5. Accordingly, it is possible to display proper recommended foot landing positions according to asymmetry of left and right foot landing timings of the user P. Therefore, it is possible to display recommended foot landing positions at proper timings in accordance with states of the feet even though one foot of the user P is injured or paralyzed. The recommended foot landing position determiner 240 may make the period T(N2) of the stride after next N2 consistent with the period T(B2) of the stride before last B2. Alternatively, the recommended foot landing position determiner 240 may set the period T(N2) of the stride after next N2 to a period between the period T(Curr) of the current stride Curr and the period T(B2) of the stride before last B2.

Figure 8:
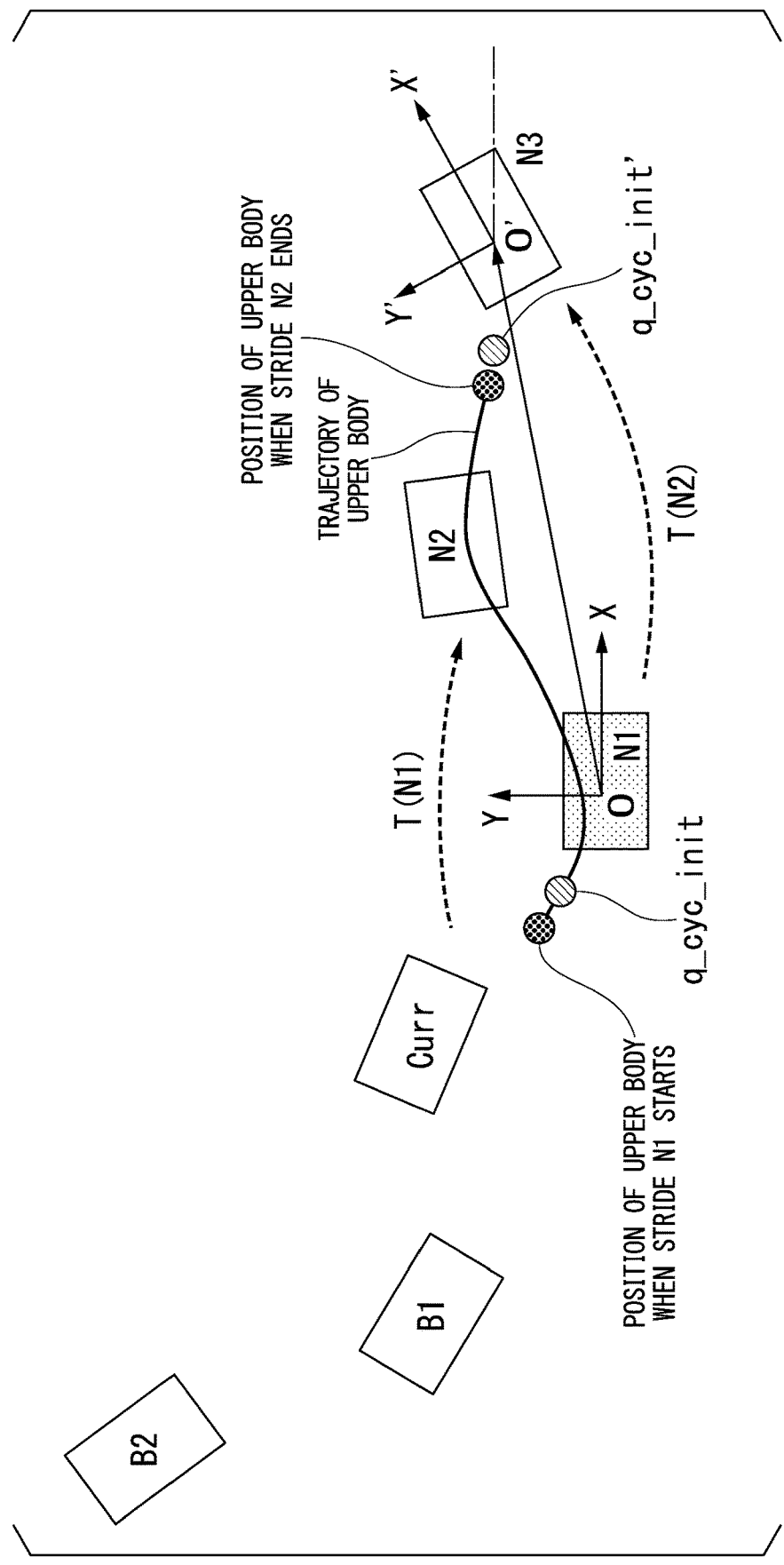
FIG. 8 is a diagram for describing an initial divergence component of a steady-state gait.

The recommended foot landing position determiner 240 obtains an initial divergence component q_cyc_init of a steady-state gait according to the current stride Curr, the next stride N1, the stride after next N2 and the second stride after next N3. FIG. 8 is a diagram for describing an initial divergence component of a steady-state gait. The recommended foot landing position determiner 240 determines an initial divergence component of a steady-state gait based on the foot landing position and the orientation (coordinate system O-X-Y of FIG. 8) of the next stride N1 as the initial divergence component q_cyc_init of the steady-state gait. Specifically, the recommended foot landing position determiner 240 obtains the initial divergence component q_cyc_init using the dynamics 271 such that the initial divergence component q_cyc_init based on the foot landing position and the orientation of the next stride N1 is consistent with an initial divergence component q_cyc_init' based on the foot landing position orientation (coordinate system O'-X'-Y' of FIG. 7) of the second stride after next N3. The recommended foot landing position determiner 240 may obtain an initial inverted pendulum material point position and velocity of the steady-state gait such that the steady-state gait continuity condition is satisfied and obtain the initial divergence component q_cyc_init of the steady-state gait from the obtained result.

Figure 9:
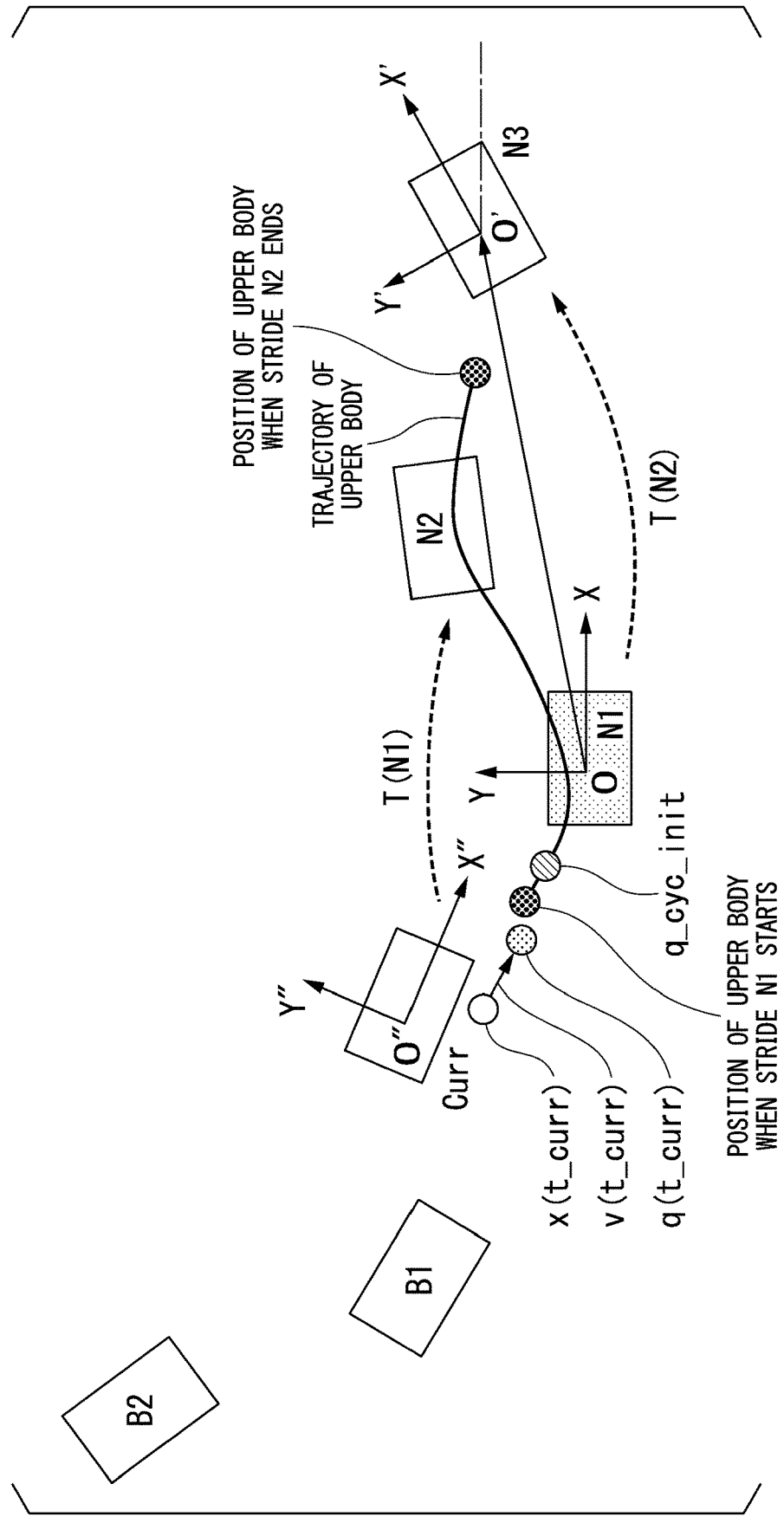
FIG. 9 is a diagram showing an example of a relationship between a centroid movement velocity V(t_curr), a centroid position X(t_curr) and a current divergence component q(t_curr).

The recommended foot landing position determiner 240 acquires a current centroid movement velocity V(t_curr) and centroid position X(t_curr), for example, through the centroid position/velocity detector 220. Next, the recommended foot landing position determiner 240 obtains a current divergence component q(t_curr) according to "q(t_curr)=x(t_curr)+v(t_curr)/$\lambda_o$" on the basis of the centroid movement velocity V(t_curr) and centroid position X(t_curr). FIG. 9 shows an example of a relationship among the centroid movement velocity V(t_curr), the centroid position X(t_curr) and the current divergence component q(t_curr).

The recommended foot landing position determiner 240 performs parallel movement of the initial divergence component q_cyc_init, the foot landing position P(N1) of the next stride N1, the foot landing position P(N2) of the stride after next N2, and the foot landing position P(N3) of the second stride after next N3 such that the initial divergence component q_cyc_init is consistent with the current divergence component q(t_curr).

Figure 10:
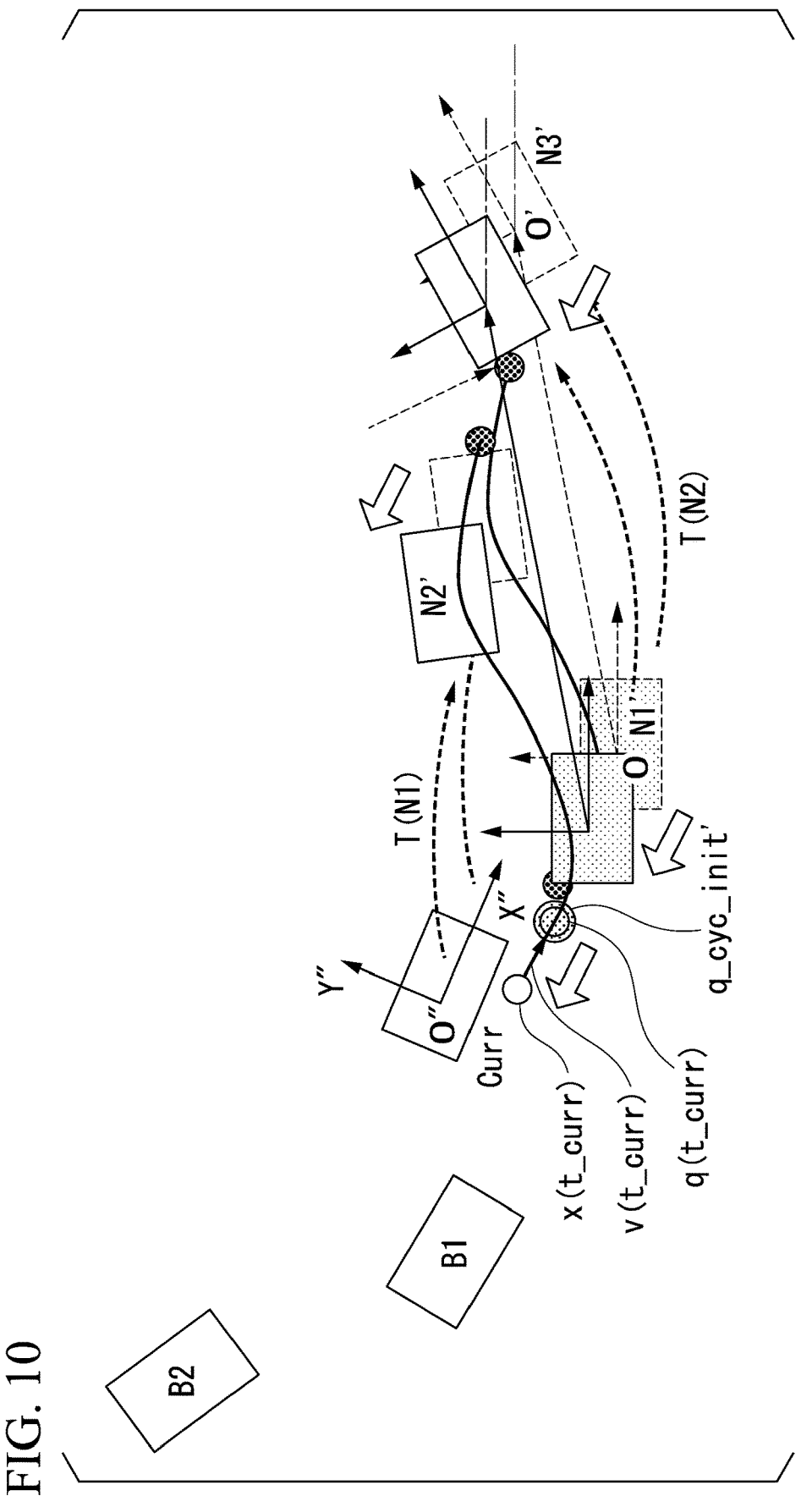
FIG. 10 is a diagram for describing parallel movement of a foot landing position.

FIG. 10 is a diagram for describing parallel movement of foot landing positions. When the initial divergence component q_cyc_init and the foot landing positions P(N1), P(N2) and P(N3) after parallel movement are respectively represented by q_cyc_init', P(N1)', P(N2)' and P(N3),' the recommended foot landing position determiner 240 acquires parallel positions thereof according to "P'(N1)=P(N1)+q(t_curr)−q_cyc_init," "P'(N2)=P(N2)+q(t_curr)−q_cyc_init," "P'(N3)=P(N3)+q(t_curr)−q_cyc_init" and "q_cyc_init'=q(t_curr)." Then, the recommended foot landing position determiner 240 determines the parallel-moved foot landing position P(N1)' of the next stride N1' as a recommended foot landing position P_aim.

Second Form Example of Recommended Foot Landing Position Determination Method

Next, a second form example of the recommended foot landing position determination method will be described. There are cases in which a delay occurs between landing of the feet of the user P and movement of a ZMP to the next foot landing position when a recommended foot landing position is displayed. Accordingly, the recommended foot landing position determiner 240 performs parallel movement of the initial divergence component q_cyc_init of the steady-state gait, the foot landing position P(N1) of the next stride N1, the foot landing position P(N2) of the stride after next N2, and the foot landing position P(N3) of the second stride after next N3 such that a divergence component estimate q(t_curr+Ta) after a predetermined time Ta from the current time is consistent with the initial divergence component q_cyc_init of the steady-state gait instead of performing parallel movement of the current divergence component q_cyc_init, the foot landing position P(N1) of the next stride N1, the foot landing position P(N2) of the stride after next N2, and the foot landing position P(N3) of the second stride after next N3 such that the initial divergence component q(t_curr) of the steady-state gait is consistent with the current divergence component q_cyc_init.

Figure 11:
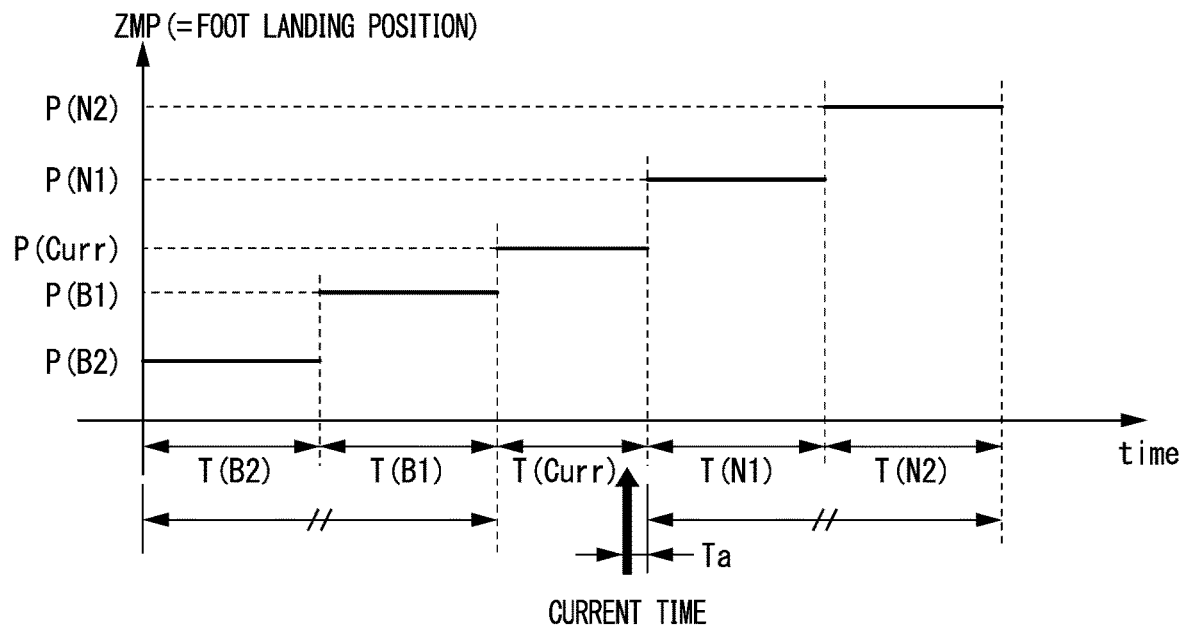
FIG. 11 is a diagram for describing a second form example of the recommended foot landing position determination method.

FIG. 11 is a diagram for describing the second form example of the recommended foot landing position determination method. The horizontal axis of FIG. 11 represents time and the vertical axis represents a ZMP (=foot landing position). The recommended foot landing position determiner 240 assumes the ZMP to be held at the current foot landing position P(Curr) and estimates the divergence component estimate q(t_curr+Ta) after the predetermined time Ta from the current time using the dynamics 271, as shown in FIG. 11. Then, the recommended foot landing position determiner 240 determines the parallel-moved foot landing position P(N1') of the next stride N1' as a recommended foot landing position P_aim.

Third Form Example of Recommended Foot Landing Position Determination Method

Figure 12:
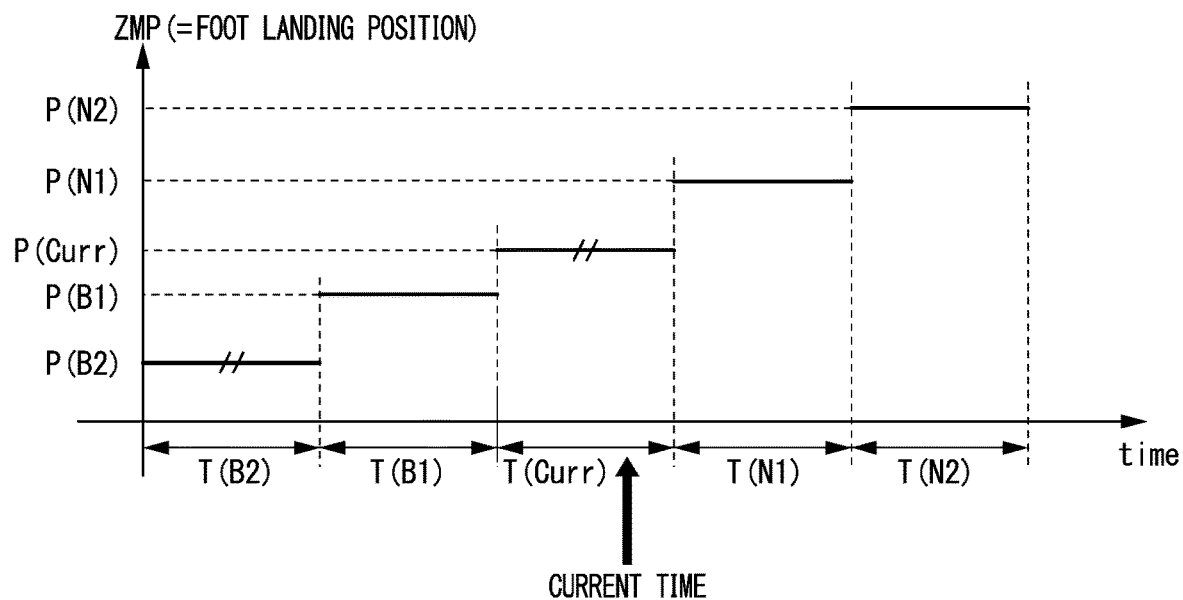
FIG. 12 is a diagram for describing a third form example of the recommended foot landing position determination method.

Next, a third form example of the recommended foot landing position determination method will be described. FIG. 12 is a diagram for describing the third form example of the recommended foot landing position determination method. The horizontal axis of FIG. 12 represents time and the vertical axis represents a ZMP (=foot landing position). A foot landing timing can be voluntarily determined by the user P in the first and second form examples of the recommended foot landing position determination method, whereas the recommended foot landing position determiner 240 also determines a next recommended foot landing timing and induces the user P to land at the recommended foot landing timing in the third form example. The recommended foot landing position determiner 240, for example, delays the next foot landing timing to be recommended (next recommended foot landing timing) by a period T(B2) from a start time of the current stride start time to a start time of the stride before last. That is, the recommended foot landing position determiner 240 makes the period T(Curr) of the current stride consistent with the period T(B2) of the stride before last, as shown in FIG. 12. The recommended foot landing position determiner 240 determines a recommended foot landing position at the next recommended foot landing timing. More specifically, the recommended foot landing position determiner 240 performs parallel movement of the initial divergence component q_cyc_init of the steady-state gait, the foot landing position P(N1) of the next stride N1, the foot landing position P(N2) of the stride after next N2, and the foot landing position P(N3) of the second stride after next N3 such that a divergence component estimate q_next_land at the next recommended foot landing timing is consistent with the initial divergence component q_cyc_init of the steady-state gait. In this case, the recommended foot landing position determiner 240 assumes the ZMP to be held at the current foot landing position P(Curr) and estimates the divergence component estimate q_next_land using the dynamics 271, as shown in FIG. 12. Then, the recommended foot landing position determiner 240 determines the parallel-moved foot landing position P(N1') of the next stride N1' as a recommended foot landing position P_aim. The display controller 250 performs display by which a remaining time from a time slightly before a recommended foot landing timing to the recommended foot landing timing is ascertained and also represents a recommended foot landing position. The recommended foot landing position is determined, for example, a predetermined time before the recommended foot landing timing. When the recommended foot landing position is displayed, it may be displayed at a fixed position until the foot landing is completed or re-calculated and displayed according to change of a divergence component of a motion every moment.

Display Screen Example

Figure 13:
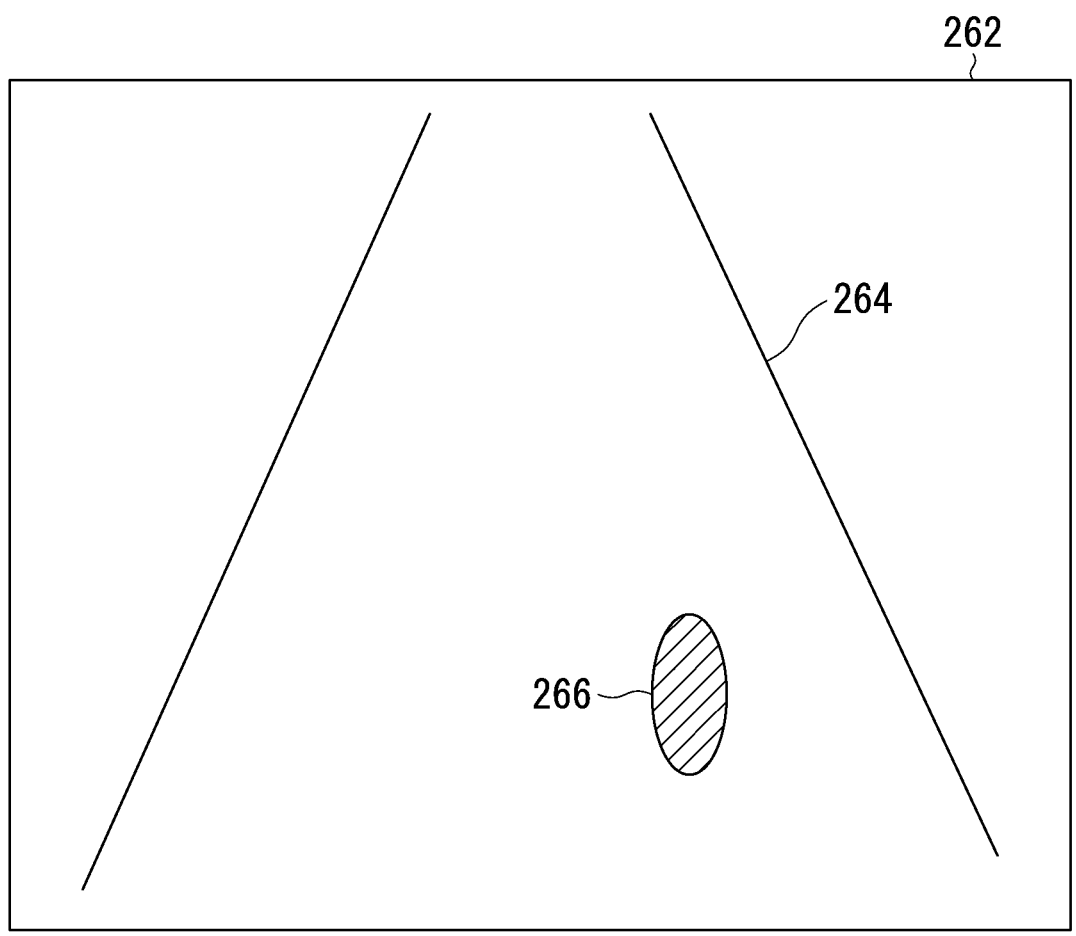
FIG. 13 is a diagram showing an example of a scene displayed on a display 260 at any moment.

Next, an example of a screen display on the display 260 will be described. FIG. 13 is a diagram showing an example of a screen displayed on the display 260 at any moment. A floor surface 264 or the like present on the real space is displayed on a screen 262 of the display 260. The display controller 250 displays an object image 266 indicating a pre-set foot landing position of the user P at a recommended foot landing position P_aim determined by the recommended foot landing position determiner 240.

The object image 266 is additionally displayed on the real space visually recognized by the user P. The object image 266 may be additionally displayed in a virtual space displayed by the display device 200. The object image 266 may be a still image composed of one frame or a moving image (video) including a plurality of frames. Accordingly, the user P can easily ascertain a foot landing position.

<Processing Flow>

Figure 14:
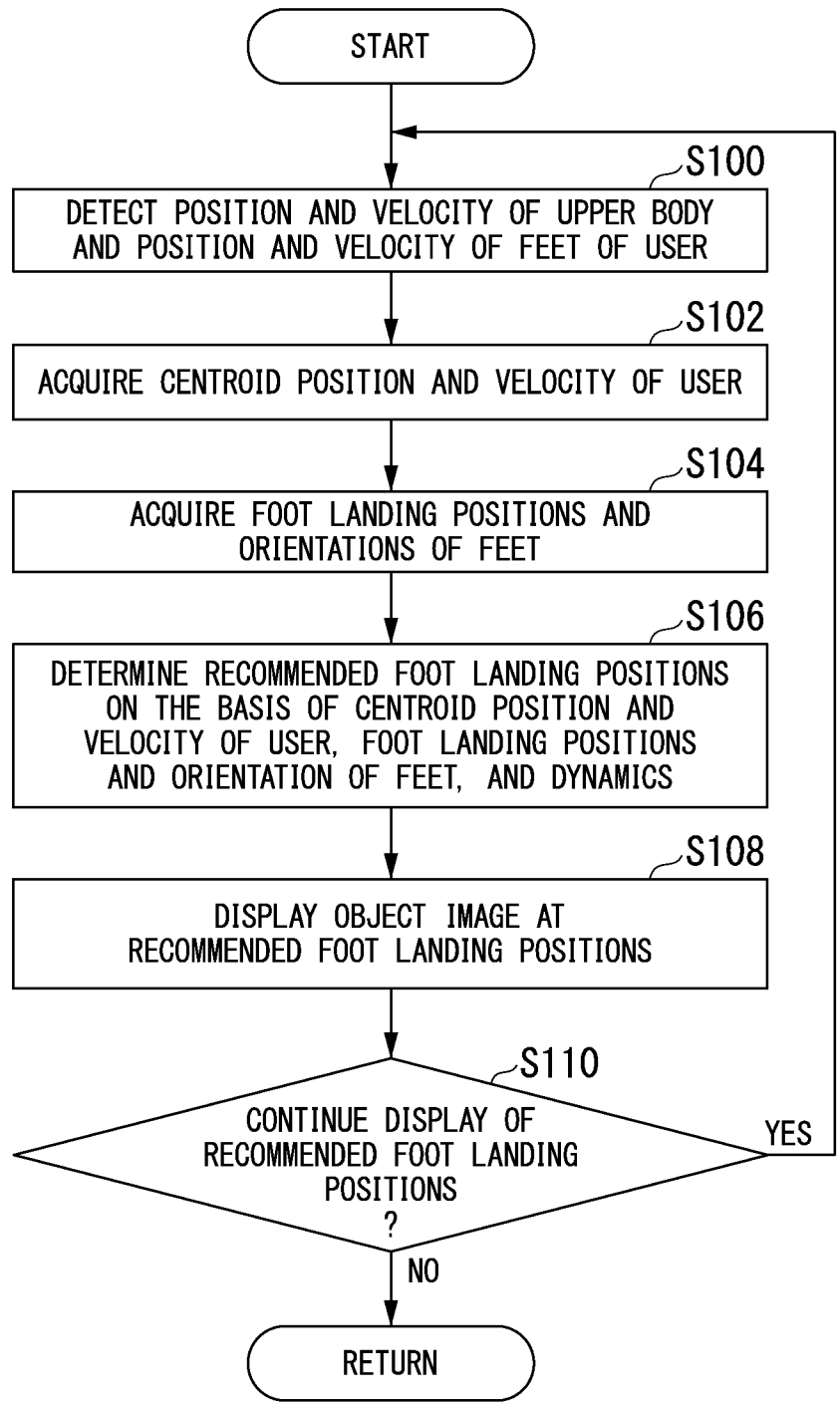
FIG. 14 is a flowchart showing an example of a flow of recommended foot landing position display processing of the first embodiment.

FIG. 14 is a flowchart showing an example of a flow of recommended foot landing position display processing of the first embodiment. First, the motion information detector 100 detects positions and velocities of the upper body and positions and velocities of the left and right feet of the user P (step S100). Next, the centroid position/velocity detector 220 calculates centroid positions and velocities of the user P on the basis of the positions and velocities of the upper body and the positions and velocities of the left and right feet of the user P (step S102). Subsequently, the foot landing position/orientation detector 230 acquires foot landing positions and orientations of the feet (step S104).

Next, the recommended foot landing position determiner 240 determines recommended foot landing positions on the basis of the centroid positions and velocities, the foot landing positions and orientations of the feet of the user P, and the dynamics 271 stored in advance in the storage 270 (step S106). Subsequently, the display controller 250 displays an object image indicating foot landing positions at positions corresponding to the recommended foot landing positions (step S108).

Next, the recommended foot landing position determiner 240 determines whether to continue display of recommended foot landing positions (step S110). For example, the recommended foot landing position determiner 240 continues display of recommended foot landing positions only in the case of the last half period of a gait. When it is determined that display of recommended foot landing positions is continued, the process returns to the process of step S100. When it is determined that display of recommended foot landing positions is not continued, the process of this flowchart ends.

Figure 15:
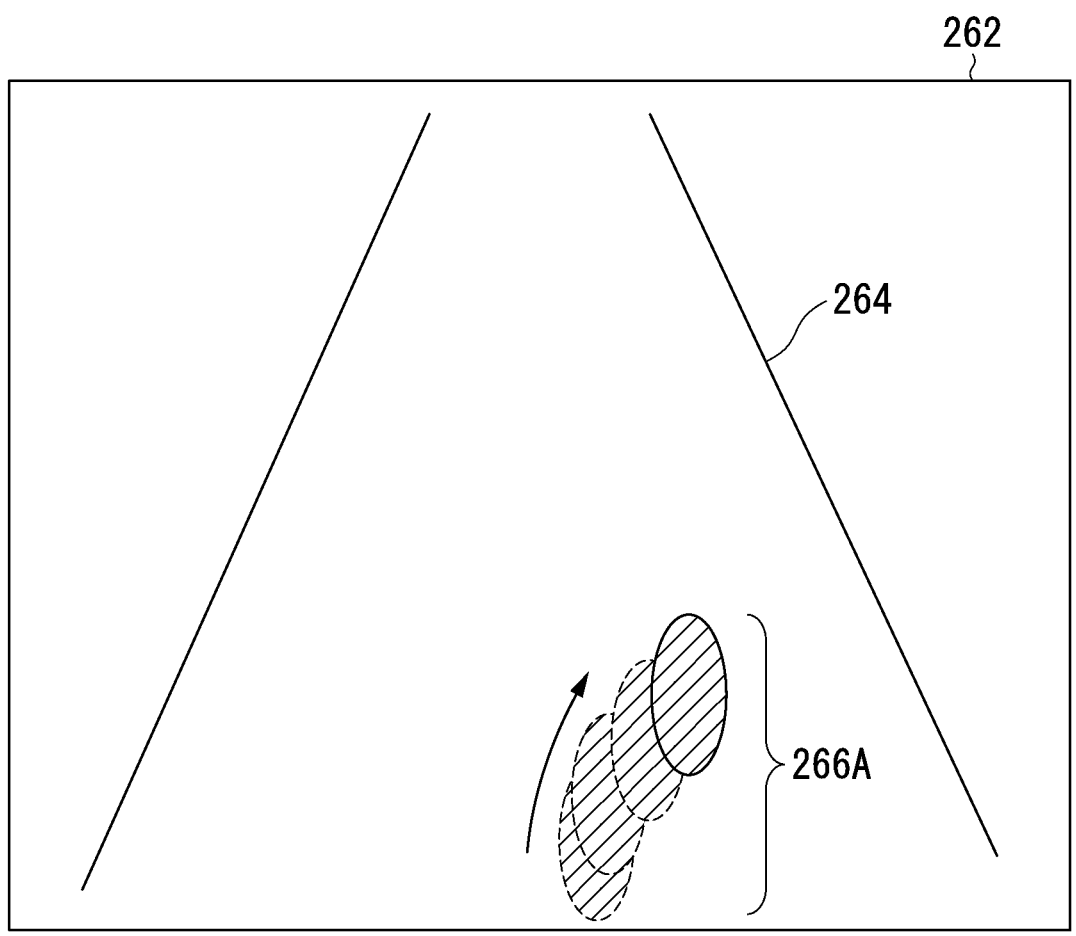
FIG. 15 is a diagram showing an example of sequential display of recommended foot landing positions.

FIG. 15 is a diagram showing an example of continuing display of recommended foot landing positions. For example, the recommended foot landing position determiner 240 repeatedly performs the process of the flowchart shown in FIG. 14 at a predetermined timing in a gait until the next foot landing point to re-determine a recommended foot landing position at each time. Accordingly, an object image 266A indicating a recommended foot landing position is continuously moved and displayed as shown in FIG. 15.

According to the above-described first embodiment, it is possible to display recommended foot landing positions of the user P acquired according to a dynamic model on the display 260 to properly guide motions of a gait of the user.

Second Embodiment

Next, a second embodiment of a walking support system will be described. Detailed description of the walking support system in the second embodiment is omitted here because the same configuration of the above-described walking support system 10 of the first embodiment can be applied thereto. In a gait on a treadmill and a gait following another person, a foot landing position is limited within a predetermined range. Accordingly, a recommended foot landing position when a foot landing position at each time is limited within a predetermined range is determined in the second embodiment. In this case, the recommended foot landing position determiner 240 determines foot landing positions of a target steady-state gait (hereinafter, there are cases in which the target steady-state gait is simply abbreviated to a "steady-state gait") on the basis of the aforementioned limitation and past foot landing positions of the user P. The recommended foot landing position determiner 240 obtains an initial divergence component of the steady-state gait and further obtains a difference between a current divergence component and the initial divergence component of the ideal steady-state gait. A difference between a current foot landing position and an ideal foot landing position is obtained.

The recommended foot landing position determiner 240 determines a correction amount of a target stride according to linear combination of these differences and determines recommended foot landing positions by adding the correction amount of the target stride to foot landing positions of the steady-state gait. The recommended foot landing position determiner 240 will be described in more detail below. Components other than the recommended foot landing position determiner 240 may be the same as those of the first embodiment.

Figure 16:
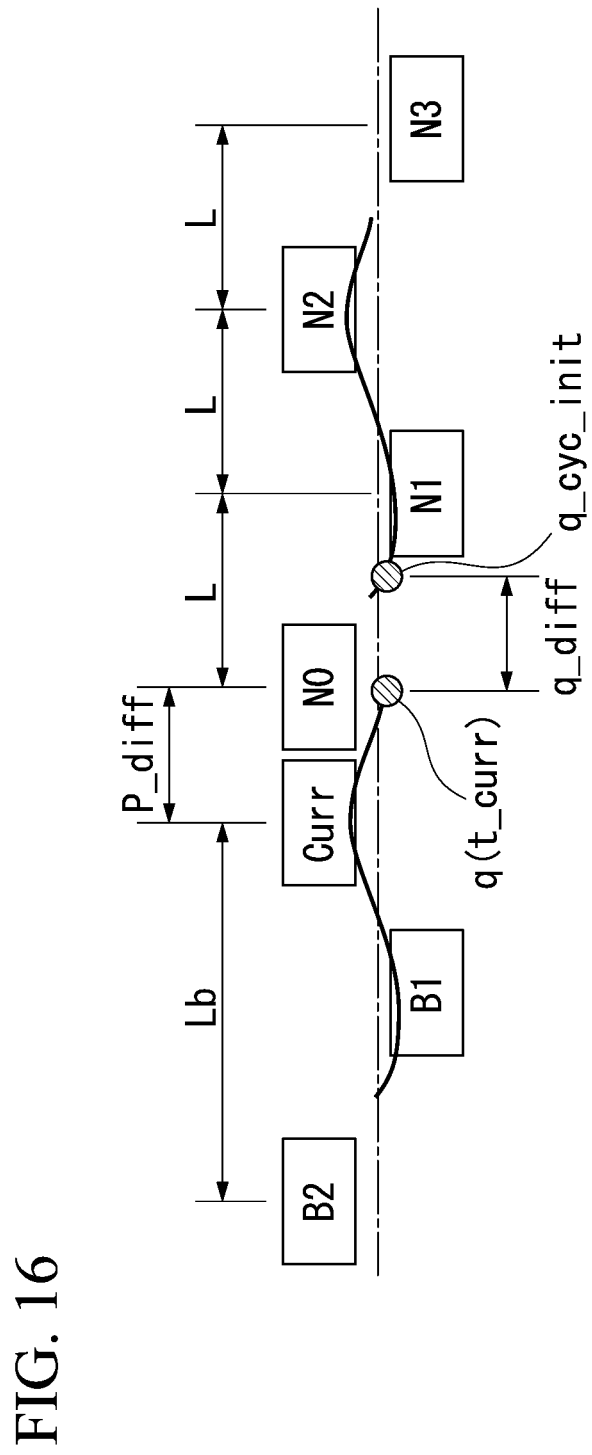
FIG. 16 is a diagram for describing a second embodiment of a walking support system.

FIG. 16 is a diagram for describing the second embodiment of the walking support system. In the example of FIG. 16, foot landing positions of gaits are represented by a rectangular form. In the second embodiment, the recommended foot landing position determiner 240 measures the foot landing position P(B2) of the stride before last, the foot landing position P(B1) of the previous stride, and the foot landing position P(Curr) of the current stride. In the second embodiment, it is assumed that the user P is walking on a movable surface of a treadmill or the like. Accordingly, it can be assumed that an orientation is consistent with a progress direction. Therefore, the walking support system 10 may not include a function of detecting a foot landing orientation in the second embodiment.

The recommended foot landing position determiner 240 determines foot landing positions P(NO), P(N1), P(N2) and P(N3) of a steady-state gait (NO, N1, N2 and N3) on the basis of a predetermined range with respect to foot landing positions and a line of past foot landing positions (e.g., a line of foot landing positions of B2, B1 and Curr). The predetermined range with respect to foot landing positions is, for example, a range in which a distance between a foot and the front end of the movable surface of a treadmill at the time of landing is equal to or greater than a predetermined distance and a distance between the foot and the rear end of the movable surface of the treadmill when the foot is separated from the floor is equal to or greater than a predetermined distance. Strides of the steady-state gait (a stride between P(NO) and P(N1), a stride between P(N1) and P(N2) and a stride between P(N2) and P(N3)) are assumed to be the same stride L. The stride L is determined to be 0.5 times the sum Lb of a stride between the stride before last B2 and the previous stride B1 and a stride between the previous stride B1 and the current stride Curr (L=Lb/2), for example.

The recommended foot landing position determiner 240 determines foot landing positions such that horizontal positions of foot landing positions (P(NO) and P(N2)) of the left leg are the same as horizontal positions of foot landing positions (P(N1) and P(N3)) of the right leg in the steady-state gait and each foot landing position of the left leg and the each foot landing position of the right leg become predetermined positions to the left and right from a certain reference line (e.g., the center line of the treadmill, or the like).

It is assumed that the current stride Curr lands at the current time. In this case, the period T(Curr) of the current stride is a time from a current stride landing time to the current time. A movement velocity of the steady-state gait is consistent with a velocity of the movable surface of the treadmill. That is, a period of one step of the steady-state gait (half of a period of one finishing gait) is determined to be L/V.

The recommended foot landing position determiner 240 obtains the current divergence component q(t_curr) and the initial divergence component q_cyc_init of the steady-state gait as in the first embodiment. If the current divergence component q(t_curr) is consistent with the initial divergence component q_cyc_init of the steady-state gait and the foot landing position P(Curr) of the current stride is consistent with the foot landing position P(NO) of the steady-state gait, it is conceivable that the user P lands at the foot landing position P(N1) at the current time so that a gait of the user P from the present time becomes close to the steady-state gait. It is conceivable that the gait of the user P from the present time becomes greatly different from the steady-state gait as a difference (hereinafter represented by q_diff) between the current divergence component q(t_curr) and the initial divergence component q_cyc_init of the steady-state gait increases. It is conceivable that the gait of the user P from the present time becomes greatly different from the steady-state gait as a difference (hereinafter represented by P_diff) between the foot landing position P(Curr) of the current stride and the foot landing position P(NO) of the steady-state gait increases.

Figure 17:
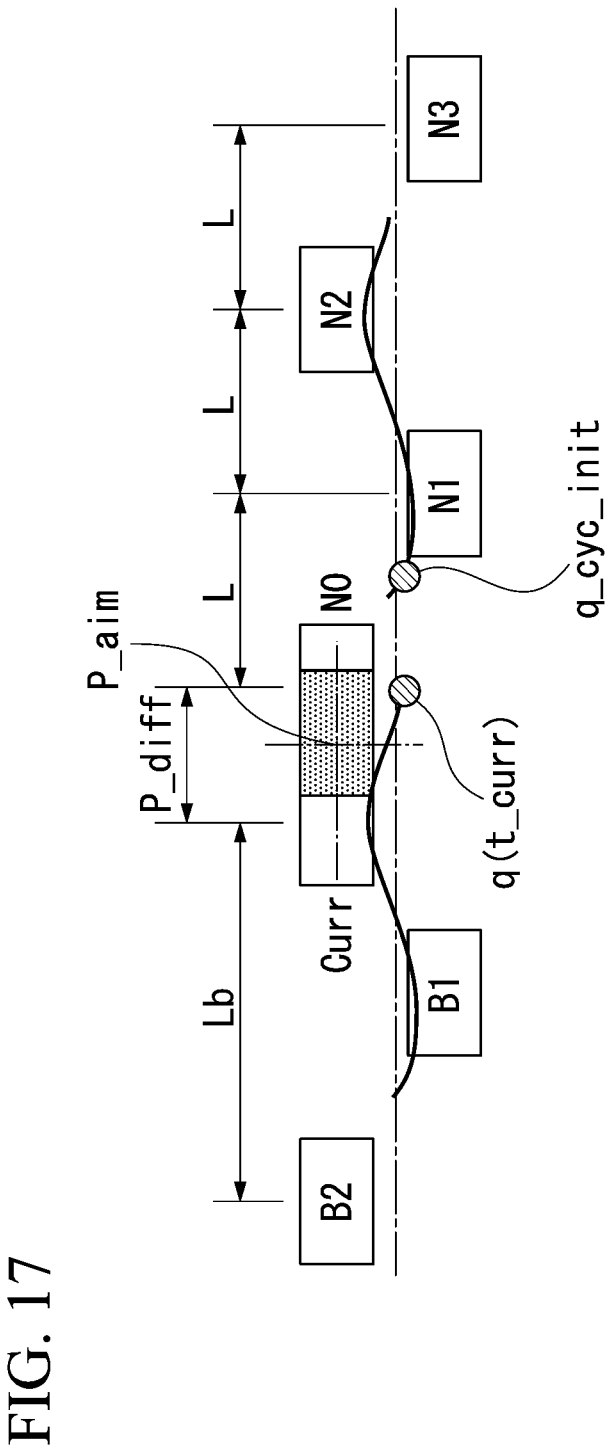
FIG. 17 is a diagram showing an example of a recommended foot landing position P_aim.

Accordingly, the recommended foot landing position determiner 240 calculates a recommended foot landing position P_aim, for example, according to "P_aim=k1*P_diff+k2*q_diff." k1 and k2 are predetermined gains, for example. FIG. 17 is a diagram showing an example of the recommended foot landing position P_aim. In the example of FIG. 17, the recommended foot landing position P_aim is represented by a rectangular shape for the foot landing position and orientation of each gait shown in FIG. 16. In this manner, divergence components of a current state (current foot landing position) and centroid (or the upper body) of the user P are fed back to determine foot landing positions in the second embodiment, and thus a centroid position of the user P can be stabilized and a foot landing position can be induced to be a proper position on the treadmill.

Third Embodiment

Figure 18:
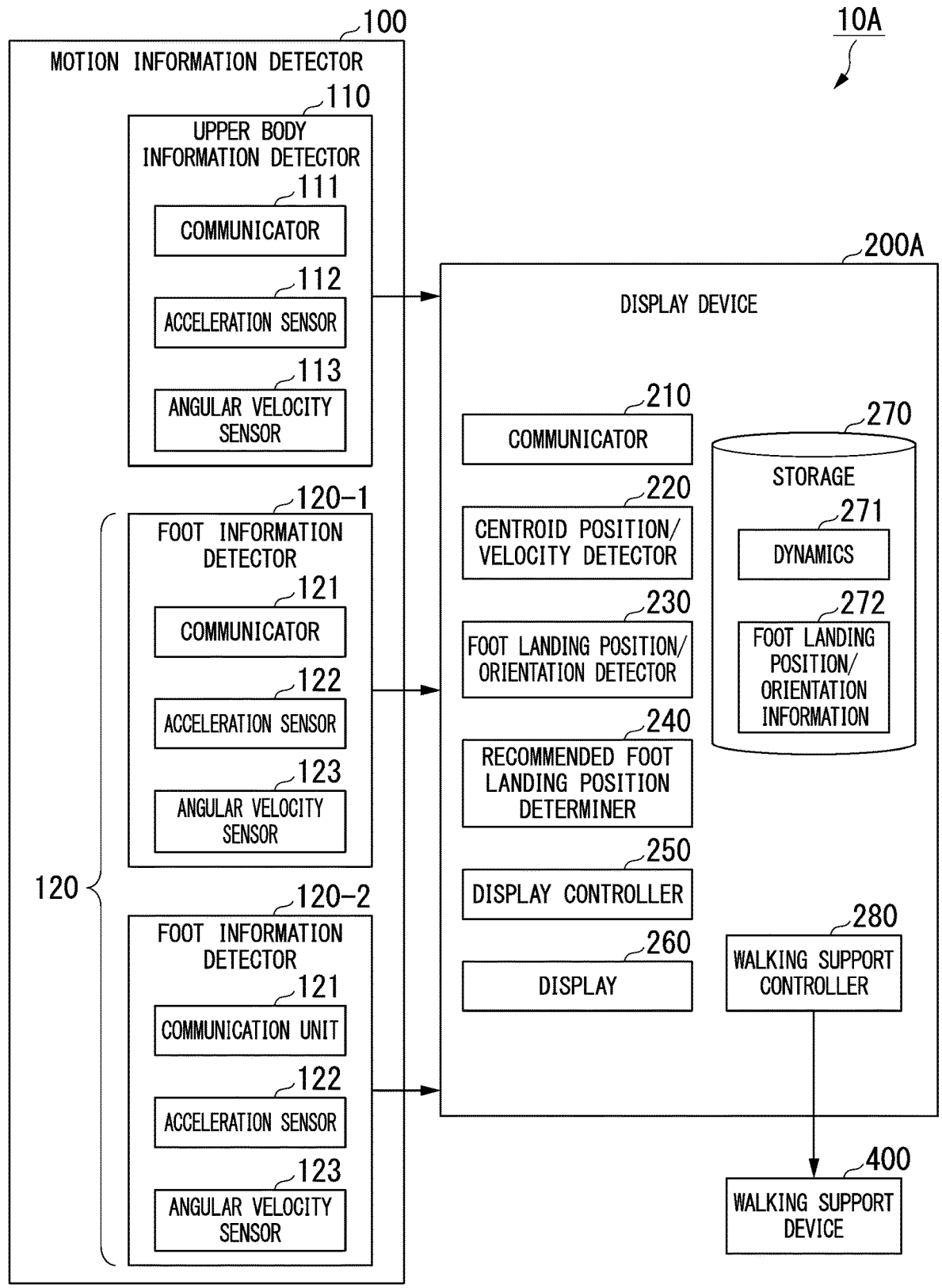
FIG. 18 is a diagram showing an example of a functional configuration of a walking support system 10A of a third embodiment.

Next, a third embodiment of the walking support system will be described. FIG. 18 is a diagram showing an example of a functional configuration of a walking support system 10A of the third embodiment. The same components as those of the walking support system 10 of the first embodiment from among the components of the walking support system 10A in the third embodiment will be attached the same signs and detailed description thereof will be omitted here.

The walking support system 10A of the third embodiment includes a walking support device 400 and includes a walking support controller 280 in the display device 200A as compared to the first embodiment. The walking support device 400 is an example of a "support device." The walking support controller 280 is an example of a "support controller." Accordingly, the following description will be based on the walking support controller 280 and the walking support device 400.

The walking support controller 280 generates control information for guiding the feet of the user P at a predetermined timing on the basis of recommended foot landing positions determined by the recommended foot landing position determiner 240 and outputs the generated control information to the walking support device 400.

The walking support device 400 is attached to the waist or feet of the user P and controls extension and flexion of the legs by driving motors of joint parts, and the like. The walking support device 400 drives the motors and guides the feet of the user P such that the user P can land on their feet at recommended foot landing positions on the basis of the control information according to the walking support controller 280.

According to the above-described third embodiment, the walking support system 10A can guide the feet of the user P to recommended foot landing positions according to the walking support device 400 in addition to creating the same effects as those of the first embodiment. Therefore, the user P can easily land on their feet close to recommended foot landing positions.

MODIFIED EXAMPLES

Here, modified examples of the above-described embodiments are described. Although the function for determining recommended foot landing positions is provided in the display device 200 in the above-described walking support system 10, the aforementioned function may be included in devices other than the display device 200. For example, if an object indicating a recommended foot landing position is projected on an actual road surface or the like, a projection device may be attached to the waist or the like of the user P and an object image indicating a recommended foot landing position may be projected from the projection device attached to the waist on a road surface instead of the display device 200. Accordingly, the user P need not mount the display device 200 on their head and thus can reduce the load of the head. If a supporter who supports a gait of the user P accompanies the user P, the supporter can also be aware of recommended foot landing positions. Accordingly, the supporter can appropriately support a gait of the user P.

The display device 200 may be a portable communication terminal such as a smartphone or a tablet terminal. In this case, the user P holds the portable communication terminal and moves their feet in accordance with recommended foot landing positions displayed on a screen of the communication terminal. The display device 200 may be included in a moving robot running with the user P. The motion information detector 100 may be included in the moving robot running with the user P.

In the walking support system 10, as information to be output to the user P, audio may be output instead of or in addition to an object image. In this case, the display device 200 includes an audio output device such as a speaker. Contents of output audio are information for guiding feet to be landed, such as "forward a little more" and "slowly," for example. Accordingly, the user P can perform a proper gait in accordance with audio information without viewing an object image. The above-described embodiments may be combined with some or all of other embodiments or modified examples.

As another modified example, a dynamic model which also considers the influence caused by change in postures of the upper body may be used as the dynamics 271 applied to the above-described first to third embodiments. The dynamic model which also considers the influence caused by change in postures of the upper body may be, for example, a dynamic model including an inverted pendulum model corresponding to a movement of the upper body in the horizontal direction and a flywheel corresponding to a rotational motion of the upper body. Accordingly, it is possible to determine foot landing positions more properly.

An another modified example, a map having a foot landing position history and current motion information of a user detected by the motion information detector 100 as inputs and having recommended foot landing positions determined by the algorithm represented in the first embodiment as outputs may be created off-line. In this case, when the user actually walks, recommended foot landing positions are determined by using the map.

Figure 19:
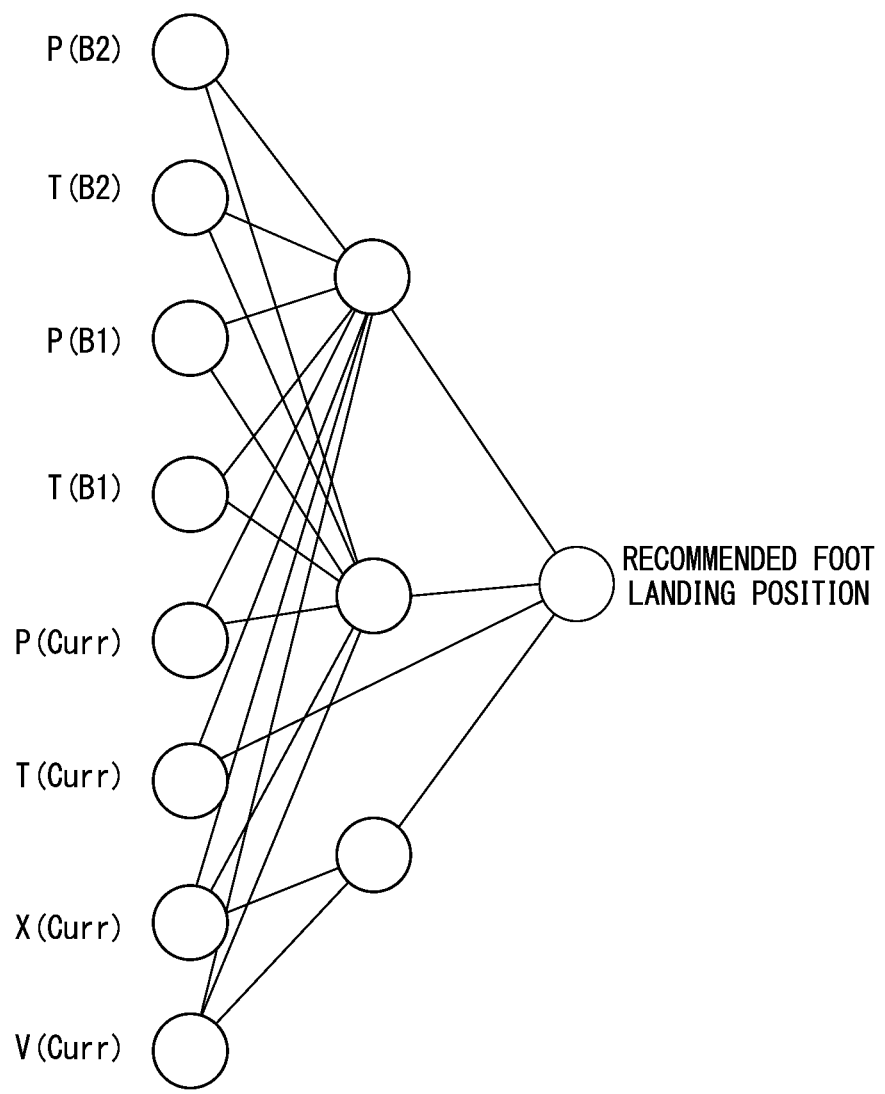
FIG. 19 is a diagram showing an example of obtaining recommended foot landing positions using a neural network.

As another modified example, the recommended foot landing position determiner 240 may detect recommended foot landing positions using a neural network. FIG. 19 is a diagram showing an example of obtaining recommended foot landing positions using a neural network. The recommended foot landing position determiner 240 may construct a neural network having a foot landing position history and current motion information of the user P detected by the motion information detector 100 as inputs and having a recommended foot landing position as an output, as shown in FIG. 19, according to deep learning, for example, and obtain recommended foot landing positions using the constructed neural network. For example, the foot landing position history may be the foot landing position P(B2) and period T(B2) of the stride before last, and the foot landing position P(B1) and period T(B1) of the previous stride. For example, the current motion information may be the foot landing position P(Curr), period T(Curr), centroid position X(Curr) and centroid movement velocity V(Curr) of the current stride.

Figure 20:
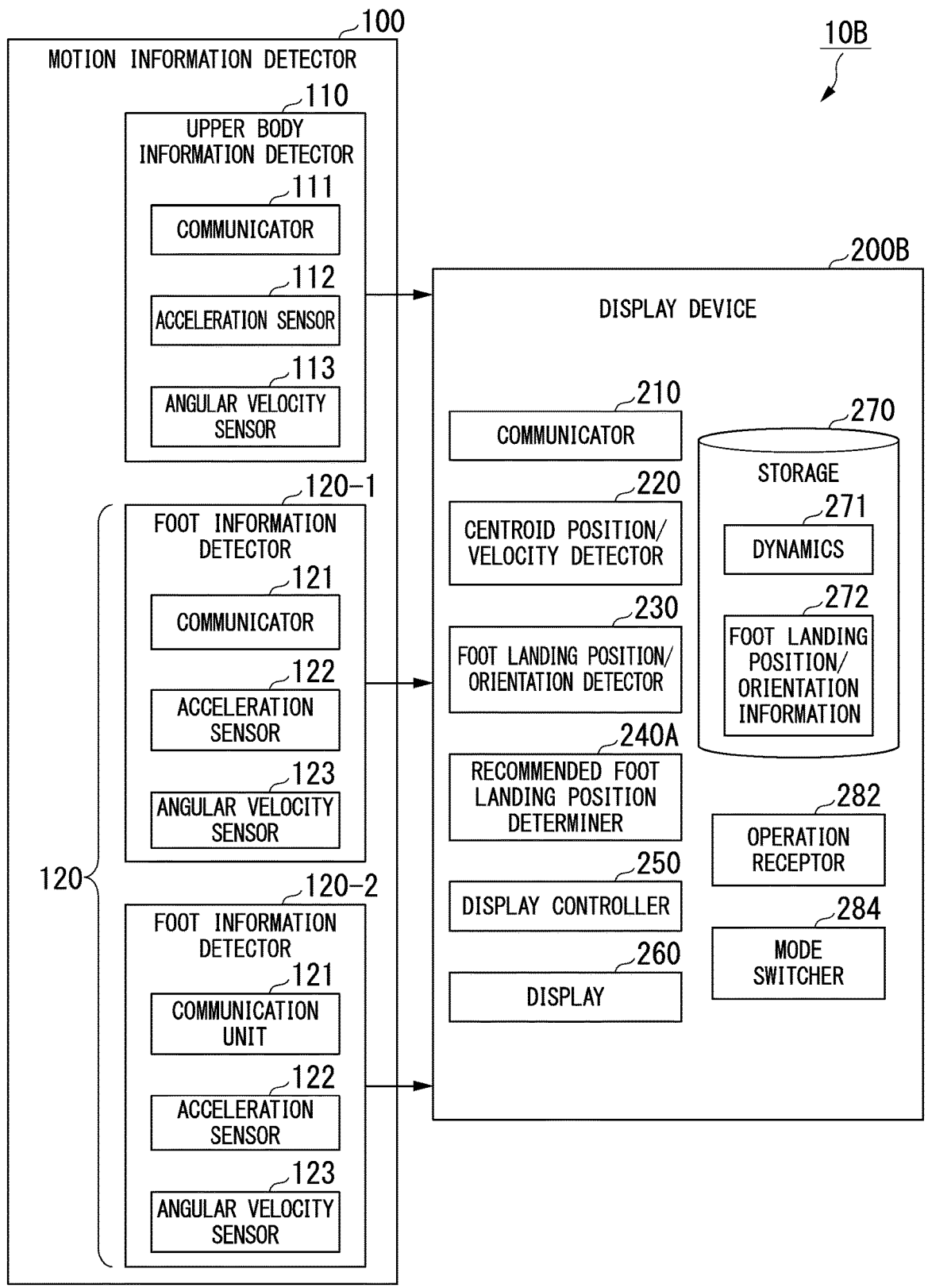
FIG. 20 is a diagram showing an example of a walking support system 10B including an operation receptor 282 and a mode switcher 284 in a display device 200B.

As another modified example, the display device 200 may include an operation receptor and a mode switcher such that a plurality of recommended foot landing positions determined according to the first to third embodiments and a plurality of display methods can be selected and displayed, instead of displaying a recommended foot landing position determined by one recommended foot landing position determination method on the display device 200 and. FIG. 20 is a diagram showing an example of a walking support system 10B including an operation receptor 282 and a mode switcher 284 in a display device 200B. In the example of FIG. 20, the same components as those of the walking support system 10 of the first embodiment are attached the same names and signs. The following description will be chiefly based on a recommended foot landing position determiner 240A, the operation receptor 282 and the mode switcher 284.

The operation receptor 282 receives operation contents from the user P. For example, the operation receptor 282 may be a mechanical switch such as a button or a switch provided in the display device 200B. The operation receptor 282 may be a graphical user interface (GUI) displayed on the display 260. The operation receptor 282 receives, for example, input of information about a display mode from the user P. When the object image 266 indicating a recommended foot landing position is displayed on the screen 262, for example, the display mode includes a first mode of displaying the object image 266 at a fixed position and a second mode of displaying the object image 266 while moving a recommended foot landing position like the object image 266A.

The mode switcher 284 performs mode switching on the basis of a display mode received by the operation receptor 282 and outputs switched mode information to the recommended foot landing position determiner 240. The recommended foot landing position determiner 240A selects any of the first to third form examples of the recommended foot landing position determination method when mode switching the first mode has been performed. The recommended foot landing position determiner 240A may select re-determination of a recommended foot landing for each moment or determination only at a predetermined moment (recommended foot landing time).

When determination is performed only at a predetermined moment (recommended foot landing time), the recommended foot landing position determiner 240A may determine a recommended foot landing position such that the recommended foot landing position is not moved with respect to the floor (display the recommended foot landing position at a fixed position with respect to the floor).

The mode switcher 284 may switch recommended foot landing position display timings, strides and the like according to the age and an injury or rehabilitation degree of the user P instead of or in addition to the first mode and the second mode.

The recommended foot landing position determiner 240 corrects a recommended foot landing position to be displayed to a position close to the user P when an operation for accelerating the movement velocity of the user P to higher than a current movement velocity has been received by the operation receptor 282. Accordingly, the user P lands on their feet at the corrected recommended foot landing position so that the centroid inclines forward and thus can perform accelerated walking. The recommended foot landing position determiner 240 corrects a recommended foot landing position to a position further away from the user P when an operation for decelerating the movement velocity of the user P to lower than the current movement velocity has been received by the operation receptor 282. Accordingly, the user P lands on their feet at the corrected recommended foot landing position so that the centroid remains behind and thus can perform decelerated walking.

According to the above-described modified forms, the walking support system 10B can receive a user operation and switch display mode of recommended foot landing positions and thus can display recommended foot landing positions through a display method which meets conditions such as the tastes and age of a user.

While forms for embodying the present invention have been described using embodiments, the present invention is not limited to these embodiments and various modifications and substitutions can be made without departing from the spirit or scope of the present invention.

REFERENCE SIGNS LIST 10, 10A, 10B Walking support system
100 Motion information detector
110 Upper body information detector
111, 121, 210 Communicator
112, 122 Acceleration sensor
113, 123 Angular velocity sensor
120 Foot information detector
200 Display device
220 Centroid position/velocity detector
230 Foot landing position/orientation detector
240 Recommended foot landing position determiner
250 Display controller
260 Display
270 Storage
271 Dynamics
272 Foot landing position/orientation information
280 Walking support controller
282 Operation receptor
284 Mode switcher
400 Walking support device

The invention claimed is:

1. A walking support system comprising:
a motion sensor configured to provide motion sensor data indicative of a motion of a user;
a foot landing sensor configured to provide foot landing sensor data indicative of a landing position of feet of the user;
a support device configured to support motions of the feet of the user; and
a processor configured to receive the motion sensor data and foot landing sensor data and to execute instructions to:
 detect the motion of the user from the motion sensor data;
 detect the landing position of the feet of the user from the foot landing sensor data;
 determine a recommended foot landing position which is a foot landing position for the feet suitable for stabilizing motions of a gait of the user based on motions of the gait of the user detected, the foot landing position detected, and dynamics stored in a storage; and
 output information indicating the recommended foot landing position determined to an information output device,
wherein the processor is configured to correct the recommended foot landing position determined based on a movement velocity, the foot landing position, and the dynamics to a position closer to the user when a current movement velocity of the user is accelerated, and to correct the recommended foot landing position determined based on the movement velocity, the foot landing position, and the dynamics to a position further away from the user when the current movement velocity of the user is decelerated, and
wherein the processor is configured to guide the feet of the user to the recommended foot landing position through the support device.

2. The walking support system according to claim 1, wherein the dynamics are a dynamic model including an inverted pendulum representing motions of an upper body or a centroid in the horizontal direction, wherein the processor is configured to determine the recommended foot landing position of the user such that motions of the user converge on a predetermined motion based on an ambulatory motion of the user, the foot landing position and the dynamic model.

3. The walking support system according to claim 2, wherein the predetermined motion is a steady-state gait.

4. The walking support system according to claim 1, wherein the processor is configured to continuously determine the recommended foot landing position in a case of a foot landing at a current time.

5. The walking support system according to claim 1, wherein the processor is configured to determine the recommended foot landing position using a map or a neural network obtained according to deep learning.

6. The walking support system according to claim 1, the processor is further configured to execute instructions to:
   detect orientations of the feet of the user with respect to a reference direction when the feet of the user have landed,
   wherein the processor is configured to determine the recommended foot landing position such that a trajectory of a centroid of a body of the user is turned in response to orientations of the feet based on the orientations detected.

7. The walking support system according to claim 1, the processor is further configured to execute instructions to:
   receive an operation from the user,
   wherein the processor is configured to switch display modes and determine the recommended foot landing position based on details of an operation received.

8. A walking support method, using a computer, comprising:
   detecting a motion of a user from a motion sensor configured to provide motion sensor data indicative of the motion of the user;
   detecting a foot landing position of the user from a foot landing sensor configured to provide foot landing sensor data indicative of the landing position of feet of the user;
   determining a recommended foot landing position which is a landing position of the feet suitable for stabilizing motions of a gait of the user based on detected motions of the gait of the user, the foot landing position, and dynamics stored in a storage;
   outputting information indicating a determined recommended foot landing position to an information output device;
   correcting the recommended foot landing position determined based on the movement velocity, the foot landing position, and the dynamics to a position closer to the user when a current movement velocity of the user is accelerated, and correcting the recommended foot landing position determined based on the movement velocity, the foot landing position, and the dynamics to a position further away from the user when the current movement velocity of the user is decelerated; and
   guiding the feet of the user to the recommended foot landing position through a support device configured to support motions of the feet of the user.

9. A non-transitory computer-readable storage medium configured to store computer-executable instructions that implement a walking support program configured to be executed by a computer to perform at least:
   detecting a motion of a user from a motion sensor configured to provide motion sensor data indicative of the motion of the user;
   detecting a foot landing position of the user from a foot landing sensor configured to provide foot landing sensor data indicative of the landing position of feet of the user;
   determining a recommended foot landing position which is a landing position of the feet suitable for stabilizing motions of a gait of the user based on detected motions of the gait of the user, the foot landing position, and dynamics stored in a storage;
   outputting information indicating a determined recommended foot landing position to an information output device;
   correcting the recommended foot landing position determined based on the movement velocity, the foot landing position, and the dynamics to a position closer to the user when a current movement velocity of the user is accelerated, and correcting the recommended foot landing position determined based on the movement velocity, the foot landing position, and the dynamics to a position further away from the user when the current movement velocity of the user is decelerated; and
   guiding the feet of the user to the recommended foot landing position through a support device configured to support of the feet of the user.

* * * * *